United States Patent
Abe et al.

(10) Patent No.: US 8,748,544 B2
(45) Date of Patent: *Jun. 10, 2014

(54) MEDICAL APPLIANCE HAVING A SLIDABLE COATING LAYER AND SYRINGE

(71) Applicant: Terumo Kabushiki Kaishi, Shibuya-ku (JP)

(72) Inventors: Yoshihiko Abe, Kanagawa (JP); Eiji Watanabe, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/042,468

(22) Filed: Sep. 30, 2013

(65) Prior Publication Data
US 2014/0031764 A1 Jan. 30, 2014

Related U.S. Application Data

(63) Continuation of application No. PCT/JP2012/057684, filed on Mar. 26, 2012.

(30) Foreign Application Priority Data

Mar. 30, 2011 (JP) .................................. 2011-075196

(51) Int. Cl.
| | | |
|---|---|---|
| C08G 77/12 | (2006.01) | |
| C08G 77/20 | (2006.01) | |
| A61L 31/10 | (2006.01) | |
| A61M 5/31 | (2006.01) | |
| A61M 5/315 | (2006.01) | |
| A61L 29/08 | (2006.01) | |

(52) U.S. Cl.
USPC ............ 525/477; 604/221; 604/265; 604/187

(58) Field of Classification Search
None
See application file for complete search history.

(56) References Cited

U.S. PATENT DOCUMENTS 4,631,321 A 12/1986 Suzuki
5,290,228 A * 3/1994 Uemura et al. ................. 604/90
(Continued)

FOREIGN PATENT DOCUMENTS

EP 0 953 675 A2 11/1999
EP 2 226 088 A1 9/2010
(Continued)

OTHER PUBLICATIONS

Notification of Transmittal of Translation of the International Preliminary Report on Patentability (Forms PCT/IB/338 and PCT/IB373) and the Written Opinion of the International Searching Authority (Form PCT/ISA/237) issued on Jun. 19, 2012, by the International Bureau of WIPO in corresponding International Application No. PCT/JP2012/057684. (10 pages).

(Continued)

*Primary Examiner* — Robert S Loewe
(74) *Attorney, Agent, or Firm* — Buchanan Ingersoll & Rooney P.C.

(57) ABSTRACT

A medical appliance including a slidable coating layer moves in contact with an inner surface of a medical member or that of a lumen. The medical appliance has the slidable coating layer formed at a part thereof which contacts the medical member or the lumen. The slidable coating layer is formed of a composition containing a solventless-type hardening silicone-based resin.

22 Claims, 4 Drawing Sheets

(56) References Cited

U.S. PATENT DOCUMENTS

| | | | |
|---|---|---|---|
| 5,352,378 A * | 10/1994 | Mathisen et al. | 508/215 |
| 6,200,627 B1 * | 3/2001 | Lubrecht | 427/2.28 |
| 6,200,915 B1 | 3/2001 | Adams et al. | |
| 6,746,430 B2 * | 6/2004 | Lubrecht | 604/230 |
| 7,111,848 B2 | 9/2006 | Tachikawa et al. | |
| 7,332,227 B2 * | 2/2008 | Hardman et al. | 428/447 |
| 7,648,487 B2 * | 1/2010 | Ito et al. | 604/230 |
| 2003/0096904 A1 | 5/2003 | Hakuta et al. | |
| 2004/0084852 A1 | 5/2004 | Tachikawa et al. | |
| 2004/0209784 A1 | 10/2004 | Hardman et al. | |
| 2006/0200084 A1 * | 9/2006 | Ito et al. | 604/230 |
| 2007/0299402 A1 | 12/2007 | Ishii et al. | |
| 2010/0069523 A1 | 3/2010 | Alvarez et al. | |
| 2010/0076158 A1 | 3/2010 | Imoto et al. | |
| 2010/0324501 A1 | 12/2010 | Horiuchi et al. | |
| 2011/0097579 A1 | 4/2011 | Mizuno et al. | |
| 2011/0236458 A1 | 9/2011 | Farrar et al. | |
| 2013/0030380 A1 | 1/2013 | Abe et al. | |

FOREIGN PATENT DOCUMENTS

| | | |
|---|---|---|
| JP | 60-181162 A | 9/1985 |
| JP | 62-32970 A | 2/1987 |
| JP | 06-183555 A | 7/1994 |
| JP | 07-138480 A | 5/1995 |
| JP | 11-350361 A | 12/1999 |
| JP | 2002-037947 A | 2/2002 |
| JP | 2002-089717 A | 3/2002 |
| JP | 2004-321614 A | 11/2004 |
| JP | 2006-167110 A | 6/2006 |
| JP | 2006-520241 A | 9/2006 |
| JP | 2006-5200241 A | 9/2006 |
| JP | 2008-000287 A | 1/2008 |
| JP | 2008-144024 A | 6/2008 |
| JP | 2009-051916 A | 3/2009 |
| JP | 2010-513664 A | 4/2010 |
| JP | 2010-535563 A | 11/2010 |
| WO | WO 2009-084646 A1 | 7/2009 |

OTHER PUBLICATIONS

International Search Report (PCT/ISA/210) mailed on Jun. 19, 2012, by the Japanese Patent Office as the International Searching Authority for International Application No. PCT/JP2012/057684.

International Search Report (Form PCT/ISA/210) issued on May 31, 2011, by the Japanese Patent Office in International Application No. PCT/JP2011/057679. (4 pages).

Notification of Transmittal of Translation of the International Preliminary Report on Patentability (Forms PCT/IB/338 and PCT/IB/373) and the Written Opinion of the International Searching Authority (Form PCT/ISA/237) issued on Nov. 22, 2012, by the International Bureau of WIPO in International Application No. PCT/JP2011/057679. (6 pages).

* cited by examiner

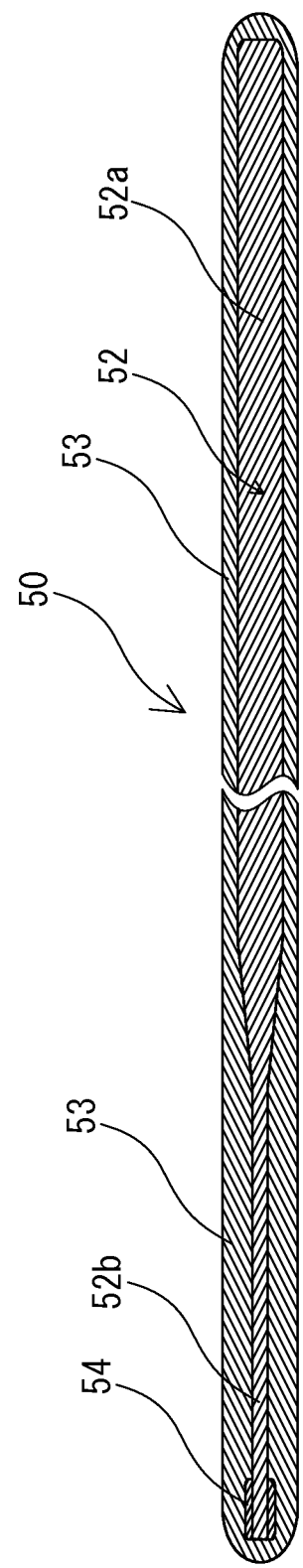

MEDICAL APPLIANCE HAVING A SLIDABLE COATING LAYER AND SYRINGE

CROSS REFERENCES TO RELATED APPLICATIONS

This application is a continuation of International Application No. PCT/JP2012/057684 filed on Mar. 26, 2012, and claims priority to Japanese Application No. 2011-075196 filed on Mar. 30, 2011, the entire content of both of which is incorporated herein by reference.

TECHNICAL FIELD

The present disclosure relates to a medical appliance with a slidable coating layer having a stable sliding performance, for example, a gasket for a syringe and a syringe having a gasket having a stable sliding performance.

BACKGROUND DISCUSSION

A prefilled syringe in which a liquid medicine is filled in advance has been used to prevent use of a wrong medical agent, prevent hospital infection, reduce waste, and increase efficiency in hospital service. Syringes including a syringe to be used as the prefilled syringe are constructed of an outer cylinder, a gasket slidable inside the syringe, and a plunger for operating the movement of the gasket respectively. To enhance the sliding performance of the gasket and obtain a high degree of flow accuracy without generating a large irregularity in the discharge of the liquid medicine from the syringe, silicone oil or the like is applied to a sliding portion of the outer surface of the gasket or the inner surface of the syringe as a lubricant. Depending on the kind of the liquid medicine, an interaction occurs between the liquid medicine and the lubricant such as the silicone oil. When the liquid medicine is stored for a long time after the liquid medicine is filled in the syringe, it is deteriorated by the interaction. Thus it is difficult to use some kinds of medical agents for the prefilled syringe.

It is desirable for the prefilled syringe that is stored for a long time with the medical agent solution being filled therein to keep the medical agent solution stable for a long time and eliminate the need for the use of the lubricant.

To address the above-described problem, as disclosed in patent document 1 (Japanese Patent Application Laid-Open No. 62-32970), patent document 2 (Japanese Patent Application Laid-Open No. 2002-089717), and patent document 3 (U.S. Pat. No. 7,111,848), prefilled syringes were proposed in which the surface of the gasket is covered with the fluorine resin which is a material having a lower friction coefficient than the material of the gasket body to eliminate the use of the lubricant.

The present applicant proposed the gasket having the coating layer composed of the fluorine resin, the silicon resin, and the urethane resin, as disclosed in a patent document 4 (Japanese Patent Application Laid-Open No. 2004-321614); and the gasket having the coating layer composed of the film made of the composition containing the sliding property-imparting component and the flexibility-imparting component and of the fine solid particles held by the film to form the rough surface on the gasket, as disclosed in patent document 5 (Japanese Patent Application Laid-Open No. 2006-167110) and patent document 6 (Japanese Patent Application Laid-Open No. 2008-287, U.S. Patent Application Publication No. 2007/0299402). As also disclosed in patent document 7 (WO Publication No. 2009-084646, U.S. Patent Application Publication No. 2010/0324501), the present applicant devised the composition containing the sliding property-imparting component, the flexibility-imparting component, and the adhesive component and proposed the gasket having the coating layer not containing the fine solid particles.

Patent document 1: Japanese Patent Application Laid-Open No. 62-32970
Patent document 2: Japanese Patent Application Laid-Open No. 2002-089717
Patent document 3: U.S. Pat. No. 7,111,848
Patent document 4: Japanese Patent Application Laid-Open No. 2004-321614
Patent document 5: Japanese Patent Application Laid-Open No. 2006-167110
Patent document 6: Japanese Patent Application Laid-Open No. 2008-287 (U.S. Patent Application Publication No. 2007/0299402)
Patent document 7: WO Publication No. 2009-084646 (U.S. Patent Application Publication No. 2010/0324501)

SUMMARY

The gaskets disclosed in patent document 1 (Japanese Patent Application Laid-Open No. 62-32970), patent document 2 (Japanese Patent Application Laid-Open No. 2002-089717, and patent document 3 (U.S. Pat. No. 7,111,848) are expected to be effective depending on a condition of use. But in a preparation for a prefilled syringe for discharging the liquid medicine therefrom under a high pressure and for having the performance of stably discharging the liquid medicine therefrom little by little with a very high accuracy for a long time by using a syringe pump or the like, liquid-tightness and sliding performance which are fundamental performance characteristics of the syringe are still in a trade-off relationship. A syringe which allows these performances to be compatible with each other at a high level and has a higher performance is desirable.

That is, in administration of the liquid medicine by using the syringe pump, when the liquid medicine is discharged therefrom in a condition where the flow rate is low (for example, in a syringe with a diameter of approximately 24 mm, a locomotive speed of the gasket is approximately 2 mm/h when a discharge speed is 1 mL/h), that the flow of the liquid medicine is invisible, an unstable discharge state called pulsation is liable to occur. Thus there is a fear that accurate administration of the liquid medicine is prevented.

The gaskets disclosed in patent document 4 (Japanese Patent Application Laid-Open No. 2004-321614) which is suggested to balance liquid-tight property with slidability, patent document 5 (Japanese Patent Publication Laid-Open No. 2006-167110), patent document 6 (Japanese Patent Application Laid-Open No. 2008-287, and U.S. Patent Application Publication No. 2007/029940) are liquid-tight and have stable sliding performance without applying a lubricant to the sliding surface thereof. However, a problem can occur in terms of production and cost in that materials forming the coating layer range widely. A problem can occur in that the solid fine particles held by the coating layer separate therefrom and the insoluble fine particles are generated in the liquid medicine. The gasket disclosed in patent document 7 (WO Publication No. 2009-084646, U.S. Patent Application Publication No. 2010/0324501) addresses these problems. But as the production principle thereof is that the reactive silicone having the silanol group at the terminal thereof is hardened in the condensation reaction by using the organic tin compound used as the catalyst to form the coating layer, the organic tin compound used as the catalyst is the essential structural requirement of the gasket of patent document 7. In recent years, owing to the problems of the poisonous property of the organic tin compound and its influence on environment, regulating the use of the organic tin compound with respect to an area or a purpose is actively considered.

According to an exemplary aspect (i.e., an aspect disclosed by way of example), provided is a medical appliance having a slidable coating layer in which a coating layer can be formed of a composition which eliminates the need for the use of an organic tin compound as a hardening catalyst and which has a stable sliding performance without applying a lubricant to a sliding surface thereof. According to an exemplary aspect, provided is a syringe including a gasket having stable sliding performance.

According to another exemplary aspect, provided is a medical appliance, comprising a slidable coating layer which moves while in contact with an inner surface of a medical member or an inner surface of a lumen, wherein said slidable coating layer is formed at a part of the medical appliance which contacts said medical member or said lumen, wherein said slidable coating layer is formed of a composition containing solventless hardening silicone-based resin.

According to a further exemplary aspect, provided is a syringe, comprising: an outer cylinder of said syringe; a gasket of said syringe which is an exemplary medical appliance having a slidable coating layer, wherein the gasket is slidably accommodated inside said outer cylinder.

An exemplary medical appliance (a medical appliance disclosed by way of example) is described below. The medical appliance moves in contact with an inner surface of a medical member or that of a lumen. The medical appliance has a slidable coating layer formed at a part thereof which contacts the medical member or the lumen. The slidable coating layer is formed of a composition containing a solventless-type hardening silicone-based resin.

An exemplary syringe has an outer cylinder for the syringe and a gasket, for the syringe, which is slidably accommodated inside the outer cylinder for the syringe. The gasket has a gasket body made of an elastic body and a slidable coating layer, formed on a part thereof which contacts at least the outer cylinder for the syringe, which is formed of the composition containing the solventless-type hardening silicone-based resin.

An exemplary medical appliance which moves in contact with the inner surface of the medical member or that of the lumen has the slidable coating layer formed at a part thereof which contacts the medical member or the lumen. The slidable coating layer is formed of the composition containing the solventless-type hardening silicone-based resin.

For example, because the slidable coating layer of the medical appliance is formed of the composition containing the solventless-type hardening silicone-based resin, the slidable coating layer can be formed of a solventless composition without using an emulsifier and without cleaning it with water. Therefore, the slidable coating layer can be formed favorably and easily. In addition, in a hardening reaction which is made in forming the coating layer, it is unnecessary to use an organic tin compound as a catalyst. Therefore in the case where the use of the organic tin compound is prohibited, the medical appliance can be stably supplied to the market.

Further, the slidable coating layer of the medical appliance has a favorable sliding property when it slides at a low speed. In addition, while the medical appliance having the slidable coating layer is in storage, the medical member (for example, outer cylinder for syringe) and the medical appliance (for example, gasket) having the slidable coating layer do not stick to each other. Therefore, a smooth initial motion can be accomplished when the syringe is used.

BRIEF DESCRIPTION OF THE DRAWINGS

FIG. 6 is a sectional view of a guide wire of an embodiment of the medical appliance having a slidable coating layer, according to an exemplary aspect.

DETAILED DESCRIPTION

An exemplary medical appliance having the slidable coating layer is described below as one example of the medical appliance disclosed here.

A medical appliance 1 moves in contact with the inner surface of a medical member or that of a lumen and has a slidable coating layer 3 formed at a part thereof which contacts the medical member or the lumen. The slidable coating layer 3 is formed of a composition which does not contain solid fine particles, but contains a solventless-type hardening silicone-based resin.

It is exemplary that the composition forming the coating layer 3 does not contain a tin-based compound. It is also exemplary that the composition forming the coating layer 3 contains a platinum group metal-based catalyst. It is exemplary that the solventless-type hardening silicone-based resin is a product of an addition reaction between silicone having at least two vinyl groups and a branch structure and silicone having at least two hydrogen groups bonded to a silicon atom. It is exemplary that the solventless-type hardening silicone-based resin is formed by hydrosilylation between the vinyl groups of the silicone having the vinyl groups and the branch structure and silicon bonded to the hydrogen groups of the silicone having the hydrogen groups bonded to the silicon atom.

The medical appliance having the slidable coating layer is described below by using an embodiment in which the medical appliance having the slidable coating layer is applied to a gasket for a syringe and to the syringe.

Figure 1:
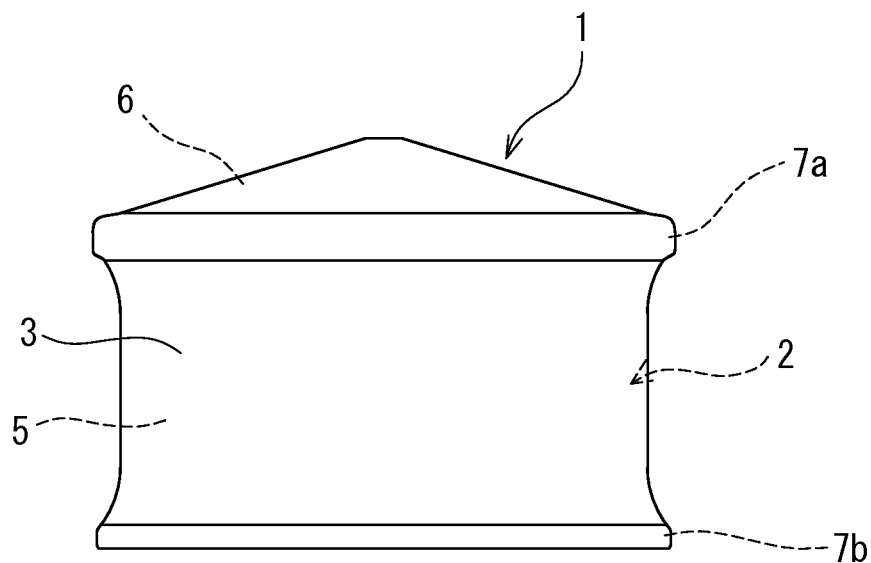
FIG. 1 is a front view of a gasket of an embodiment of a medical appliance having a slidable coating layer, according to an exemplary aspect.
Figure 2:
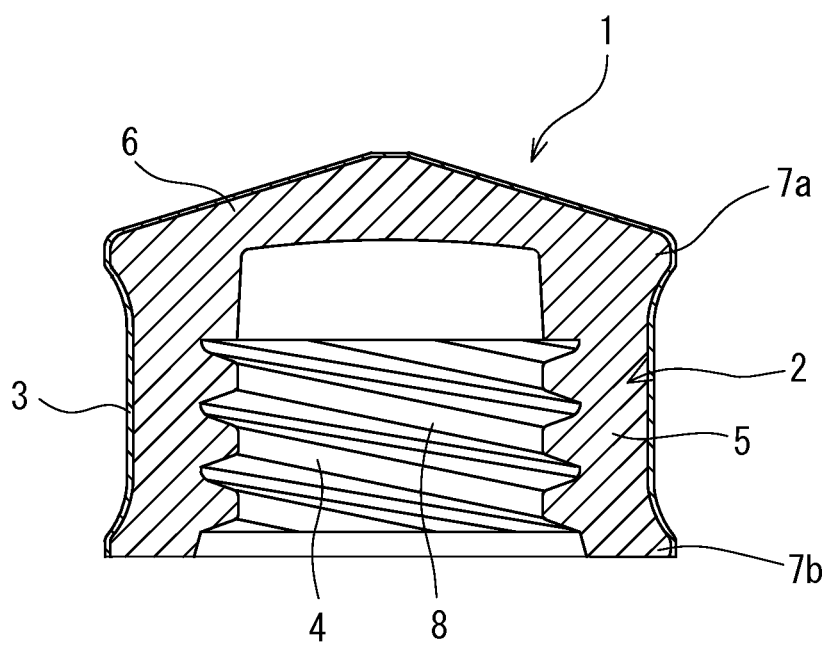
FIG. 2 is a sectional view of the gasket shown in FIG. 1, according to an exemplary aspect.
Figure 3:
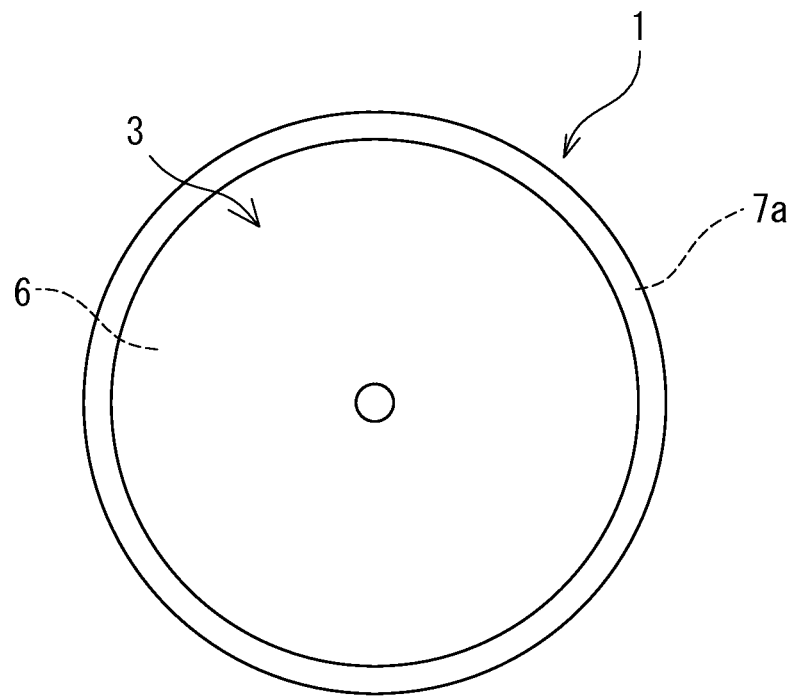
FIG. 3 is a plan view of the gasket shown in FIG. 1, according to an exemplary aspect.
Figure 4:
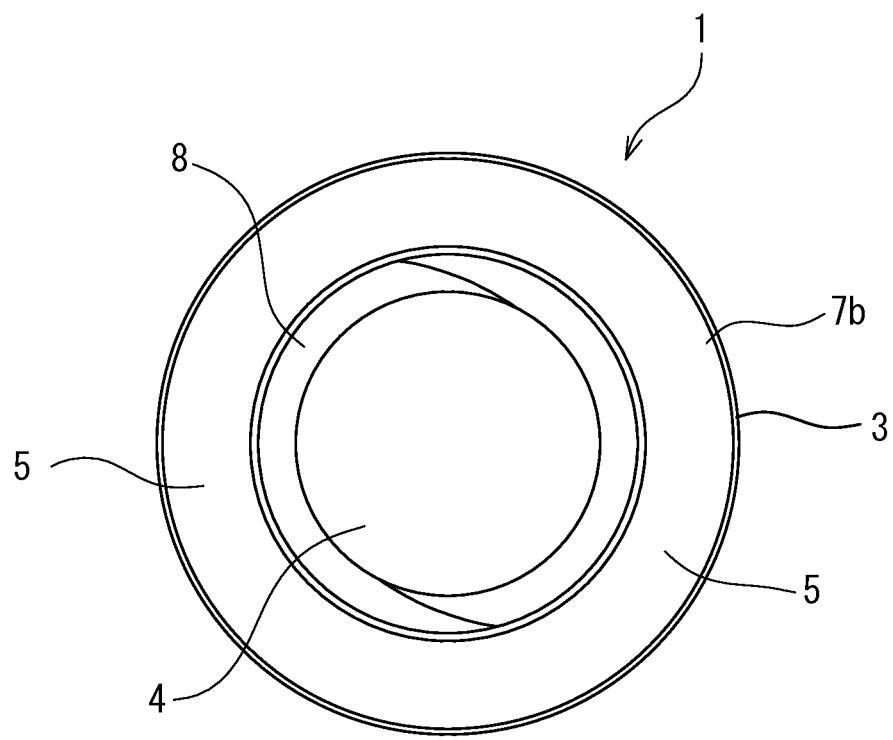
FIG. 4 is a bottom view of the gasket shown in FIG. 1, according to an exemplary aspect.
Figure 5:
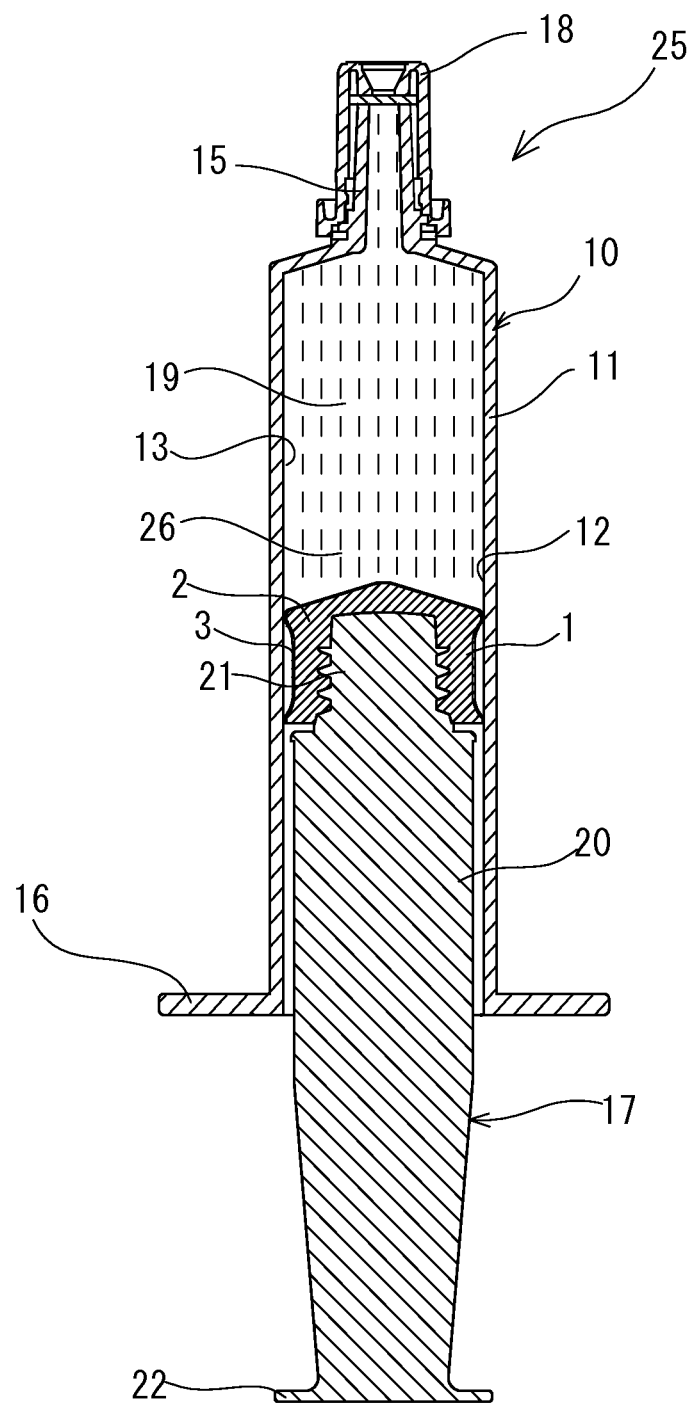
FIG. 5 is a sectional view of a prefilled syringe in which the gasket shown in FIG. 1 is used, according to an exemplary aspect.

The gasket of an exemplary embodiment is described below. FIG. 1 is a front view showing the gasket of the embodiment. FIG. 2 is a sectional view of the gasket shown in FIG. 1. FIG. 3 is a plan view of the gasket shown in FIG. 1. FIG. 4 is a bottom view of the gasket shown in FIG. 1. FIG. 5 is a sectional view of a prefilled syringe in which the gasket shown in FIG. 1 is used.

The medical appliance of this embodiment having the slidable coating layer is a gasket 1 for a syringe and liquid-tightly and slidably accommodated inside an outer cylinder 11, for the syringe, which is a medical member.

The gasket 1 which is the medical appliance slidably contacts the inside of the outer cylinder of the syringe and has the coating layer 3 formed at the part thereof which contacts the syringe. The coating layer 3 is formed of the composition which does not contain the solid fine particles and contains the solventless-type hardening silicone-based resin.

Because the coating layer of the gasket of this embodiment is formed of the above-described composition, the coating layer has a more favorable sliding performance than a coating layer containing fine particles when the gasket slides at a low speed and in addition, the gasket does not stick to the syringe during the storage of the syringe. Therefore when the syringe is used, a smooth initial motion of the gasket can be accomplished. Thus a rapid injection of a medical agent can be avoided, and the medical agent can be injected at a constant speed.

Even in a sucking operation to be often performed to check whether a blood vessel has been secured, there is the possibility of the separation of the fine particles in the case of a gasket having the coating layer containing the fine particles. On the other hand, because the fine particles are not contained in the coating layer of the gasket of an exemplary embodiment, the gasket has a merit in that there is no risk of floating of the fine particles in a liquid medicine.

The gasket 1 of this embodiment is used for the syringe and liquid-tightly and slidably accommodated inside the outer cylinder 11 for the syringe. The gasket 1 has the coating layer 3 disposed at the part thereof where the coating layer 3 contacts the outer cylinder 11. The coating layer 3 contains the specific silicone-based resin to be described later. The gasket 1 has a body part (in other words, a core part) 2 and the coating layer 3 formed on at least the part, of an outer surface of the core part 2, where the coating layer 3 contacts an inner surface 12 of the outer cylinder 11. The coating layer 3 may be formed on the entire outer surface of the core part 2.

As shown in FIGS. 1, 2, and 5, the core part 2 of the gasket 1 for the syringe has a body portion 5 extending in an almost equal diameter, a tapered portion 6 disposed at a distal side of the body portion 5 and decreasing taperingly to the distal end thereof in its diameter, a plunger-mounting portion 4 disposed inside the body portion 5 from a proximal end thereof toward the distal end thereof; a distal-side annular rib 7a disposed on a side surface of a distal portion of the body portion 5, and a proximal-side annular rib 7b disposed on a side surface of a proximal portion of the body portion 5. As shown in FIGS. 2 and 4, the plunger-mounting portion 4 is formed as an approximately columnar concave portion which is disposed inside the body portion 5 and extends from the proximal end of the body portion 5 to a position in the vicinity of the distal end thereof. A screwing portion 8 capable of screwing on a screwing portion formed at a distal end of a plunger 17 is formed on a side surface of the above-described concave portion. A distal-end surface of the concave portion is formed almost flatly. The plunger-mounting portion 4 does not necessarily have to be formed as the screwing portion, but may be formed as an engaging portion which engages the distal portion of the plunger or may be formed in combination of the screwing portion and the engaging portion. An operation of mounting the plunger on the plunger-mounting portion is performed by screwing the plunger on the plunger-mounting portion. A state in which the engaging portion has engaged the distal portion of the plunger may be held by an engaging portion formed separately from the screwing portion.

The outer diameters of the annular ribs 7a and 7b are formed a little larger than the inner diameter of the outer cylinder 11 for use in the syringe. Therefore, the annular ribs 7a and 7b compressively deform inside the outer cylinder 11. In this embodiment, two annular ribs are formed, but one or three or more annular ribs may be formed.

As materials composing the core part (body part of gasket) 2, an elastic material is exemplary. The elastic material to be used for the core part 2 is not limited to a specific one, but rubber materials (for example, vulcanized rubber materials) such as natural rubber, isoprene rubber, butyl rubber, chloroprene rubber, nitrile-butadiene rubber, styrene-butadiene rubber, and silicone rubber; styrene-based elastomers and hydrogenated styrene-based elastomers; and mixtures of the styrene-based elastomers and polyolefins such as polyethylene, polypropylene, polybutene, and α-olefin copolymers; mixtures of the styrene-based elastomers and oil such as liquid paraffin, process oil; and mixtures of the styrene-based elastomers and powdery inorganic substances such as talc, cast, mica, and the like can be used. Further, it is possible to use polyvinyl chloride-based elastomers, olefin-based elastomers, polyester-based elastomers, polyamide-based elastomers, polyurethane-based elastomers, and mixtures of these elastomers as materials composing the core part 2. As the composing material, the butyl rubber is exemplary from the standpoint that it has elastic properties and can be sterilized by a high-pressure steam. The diene-based rubber and the styrene-based elastomers are exemplary from the standpoint that these substances can be sterilized by γ rays and electron beams.

The coating layer 3 is formed at least at the portions where the annular ribs are disposed. For example, the coating layer 3 is formed at the distal-side annular rib 7a and the proximal-side annular rib 7b. The coating layer 3 may be formed on the entire outer surface of the core part 2. The thickness of the coating layer 3 is favorably 1 to 30 μm, for example, 3 to 10 μm. For example, when the thickness of the coating layer 3 is not less than 1 μm, the coating layer 3 displays a desirable slidable performance. For example, when the thickness of the coating layer 3 is not more than 30 μm, the coating layer 3 does not adversely affect the elasticity of the gasket. The coating layer 3 does not contain the solid fine particles.

The coating layer 3 is composed of a resin including a material having a lower friction coefficient than the elastic material composing the core part 2. The resin of the coating layer 3 is silicone-based. Regarding a solvent-based coating solution including a silicone-based resin dissolved in an organic solvent, there is a concern about the influence to be given thereby on the material of the gasket and another concern about the presence of a residual solvent. A water-based coating solution emulsified and dispersed in water has a problem that, for example, it is necessary to clean a formed film with water because the water-based coating solution contains an emulsifier and another problem that a small amount of the emulsifier which remains in the film deteriorates the effectiveness of a medical agent. Because both the solvent-based coating solution and the water-based coating solution are applied to the surface of the coating layer as a spray, both coating solutions are unavoidably scattered to production environments. Thus both coating solutions deteriorate the degree of cleanliness in the production environment and have a high degree of manufacturer's health hazard. Therefore, a solventless coating solution (solventless-type hardening silicone) in which neither a solvent nor water is used is exemplary.

The coating layer 3 is formed of the silicone-based resin to be obtained by hardening the reactant formed as a result of the addition reaction made between the silicone having the vinyl group and the silicone-based resin having the hydrogen group by using the catalyst including platinum. The coating layer 3 does not contain the solid fine particles. As the types of the silicone-based resin, thermosetting silicone and room-temperature curing silicone are exemplary. From the standpoint of workability, the thermosetting silicone is exemplary.

The coating layer 3 formed on the gasket does not contain the "solid fine particle". The "solid fine particle" herein means a particle having a size to such an extent as to affect the roughness of the outer surface of the coating layer 3 when the coating layer 3 is formed. Specifically, the "solid fine particle" means a particle having a diameter larger than 10% of the thickness of the coating layer 3.

Because the gasket 1 has the above-described coating layer 3, the gasket 1 has a stable sliding performance without applying a lubricant to the sliding surface thereof and is capable of maintaining sealing performance inside the medical agent accommodation space. It is exemplary that the initial sliding resistance value of the coating layer (in other words, gasket having coating layer) is not more than a maximum value of the dynamic sliding resistance value thereof. The gasket satisfying the above-described requirement is capable of starting favorable initial sliding and does not make an excessive initial movement.

An exemplary method of forming the coating layer 3 is described below. In the method of forming the coating layer, a film composing the coating layer is obtained by applying a coating solution to the clean surface of the gasket and thereafter hardening it. At this time, as the method of applying the coating solution to the surface of the gasket, it is possible to use suitable methods such as a dipping method, a spraying method, and the like. It is exemplary to apply the coating solution as a spray (spray application) to the surface of an object to be coated with the object being rotated (for example, at 100 to 600 rpm). In applying the coating solution as a spray to the surface of the gasket, it is exemplary to do so after heating a portion of the gasket to be coated to 60 to 120 degrees C. The coating solution rapidly fixes to the surface of the portion of the gasket to be coated to form the film.

The method of hardening the coating solution can differ depending on the properties of solutions. For example, the coating solution may be left at a normal temperature, but it is exemplary to harden it by heating it. The method of thermally hardening the coating solution is not limited to a specific method, provided that the base material of the gasket is not modified or deformed. Hot-air drying, and a drying oven using infrared rays, and the like are exemplified. Alternatively, the method of hardening the coating solution can be carried out by suitable methods such as a method of using a decompression drier. The thickness of the coating layer can be 1 to 30 μm, for example, 3 to 10 μm. Such a coating layer can be easily formed by appropriately controlling the concentration of the coating solution which is a mixed solution, the dipping method or the spraying method.

As the coating solution, a solventless coating solution (solventless-type hardening silicone) in which neither a solvent nor water is used is exemplary. To prevent the coating layer 3 from peeling off the gasket body (the core part) or the coating layer 3 from being destroyed when the gasket slides, the coating solution is prepared so that the coating solution makes a reaction to form a specific silicone-based resin. To this end, it is exemplary that the coating solution contains not only reactive silicone, but also an auxiliary agent for obtaining adhesion between the coating layer 3 and the core part 2 and enhancing the strength of the coating layer.

The solventless coating solution to be used in an exemplary aspect is described below. Components of the coating solution can be classified into three kinds. They are a component 1 which is the reactive silicone, a component 2 serving as a reaction catalyst for the component 1 and a component 2 which is behaved as a reaction inhibitor if desired, and a component 3 which is the auxiliary agent for preventing the coating layer 3 from peeling from the core part 2 and from being destroyed. The coating solution is capable of containing additives as desired.

It is exemplary to set the viscosity of the coating solution to not more than 30 to 500 mPa·s at 25 degrees C. before it hardens. It is difficult to make preparation for the coating solution having a viscosity less than 30 mPa·s. For example, when the coating solution having a viscosity not less than 500 mPa·s is used, the coating layer 3 has a thickness not less than 50 μm and thus has a large sliding resistance value. The viscosity can be measured at 25 degrees C. by using a vibration type viscometer (VM-100A produced by SEKONIC Corporation).

Each component is described in detail below.

The component 1 is polysiloxane contained as the main component of the silicone-based resin of the coating layer 3. The component 1 can include a combination of two kinds of components (component 1a, component 1b).

The component 1a including polysiloxane has at least two vinyl groups in one molecule thereof and a branch structure. The viscosity of the component 1a at 25 degree C. is 30 to 1,000 mPa·s to allow the coating solution to be easily applied to the surface of the base material of the gasket as a spray. In the case where the coating layer 3 is formed of the polysiloxane having a straight-chain structure, it is difficult to allow the coating layer 3 to have a predetermined thickness by applying the coating solution to the surface of the base material of the gasket as a spray or by coating, because the polysiloxane has a very high viscosity. Thus, in such case, it is beneficial to use the form of aqueous emulsion or a solvent.

In this embodiment, as the component 1, the polysiloxane having the branch structure is used. The use of the polysiloxane having the branch structure can prevent the coating solution from having a higher viscosity than that of a coating solution containing the polysiloxane having the straight-chain structure, supposing that the polysiloxane having the branch structure and the polysiloxane having the straight-chain structure have an equal molecular weight, but allows the coating solution containing the polysiloxane having the branch structure to have a low viscosity. Thus, the use of the polysiloxane having the branch structure can eliminate the need for a solvent in forming the coating solution. To adjust the viscosity of the component 1a, the straight-chain structure polysiloxane having the vinyl group at both terminals thereof may be mixed with the branch structure polysiloxane.

The silicone (polysiloxane) having at least two vinyl groups and the branch structure can be prepared by performing a thermal reaction between 1,5-diethenyl-3,3-bis[(ethenyldimethylsilyl)oxy]-1,1,5,5-tetramethylpentanetrisiloxane, 1,3,5,7-tetravinyltetramethylcyclotetrasiloxane, and/or octamethylcyclotetrasiloxane in the presence of an acid catalyst such as trifluoromethanesulfonic acid at 80 to 120 degrees C., for example, 80 to 90 degrees C. for several hours, neutralizing the acid catalyst with calcium carbonate or the like, and removing a low boiling-point substance from the filtrate.

It is exemplary that the silicone (polysiloxane) having at least two vinyl groups and the branch structure is formed by polymerizing the 1,3,5,7-tetravinyltetramethylcyclotetrasiloxane and/or the octamethylcyclotetrasiloxane with the 1,5-diethenyl-3,3-bis[(ethenyldimethylsilyl)oxy]-1,1,5,5-tetramethylpentanetrisiloxane.

The component 1b is polysiloxane contained as an auxiliary component of the silicone-based resin of the coating layer 3 and reacts with the polysiloxane contained in the component 1a which is the main component of the silicone-based resin of the coating layer 3, thus playing the role of a crosslinking agent in the silicone-based resin. The polysiloxane of the component 1b has at least two hydrogen groups bonded to the same silicon atom in one molecule thereof. As the polysiloxane having at least two hydrogen groups bonded to the silicon atom in one molecule thereof, polymethylhydrosiloxane having the trimethylsilyl group at both terminals thereof, poly(methylhydrosiloxane-dimethylsiloxane) having the trimethylsilyl group at both terminals thereof, polyethylhydrosiloxane having the trimethylsilyl group at both terminals thereof, and poly(methylhydrosiloxane-octylmethylsiloxane) having the trimethylsilyl group at both terminals thereof are listed.

As a chain extender as well as the crosslinking agent, it is possible to add polydimethylsiloxane having the hydrogen group at both terminals thereof, polyphenyl(dimethylhydrosiloxy)siloxane having the hydrogen group at both terminals thereof, and poly(methylhydrosiloxane-phenylmethylsiloxane) having the hydrogen group at both terminals thereof to the polysiloxane.

The viscosity of the polysiloxane of the component 1b can be 2 to 100 mPa·S, for example, 10 to 50 mPa·S. For example, the content (relative to silicon) of the hydrogen group bonded to the silicon atom is 100 mol % in the case of the polymethylhydrosiloxane having the trimethylsilyl group at both terminals thereof, 3 to 50 mol % in the case of the poly(methylhydrosiloxane-dimethylsiloxane) having the trimethylsilyl group at both terminals thereof and the poly(methylhydrosiloxane-octylmethylsiloxane) having the trimethylsilyl group at both terminals thereof, and 0.01 to 0.5 wt % in the case of the polysiloxane having the hydrogen group at both terminals thereof. As the mixing amount of the component 1b to be contained in the coating solution, the amount of the hydrogen group of the component 1b relative to the amount of the vinyl group of the component 1a is 0.5 to 2.0, for example, 0.8 to 1.5 in the mole rate.

The component 2 serves as the catalyst in the reaction between the component 1a and the component 1b as one of its roles. As the reaction catalyst, the component 2 consists of the platinum-group metals for accelerating the hydrosilylation between the vinyl group of the component 1a and the hydrogen group of the component 1b. As the platinum-group metal catalyst, catalysts of platinum group, palladium group, and rhodium group are listed. Of the above-described catalysts, the platinum group catalyst is exemplary. Specifically, chloroplatinic acid, alcohol-modified chloroplatinic acid, chloroplatinic acid-ketones complexes, a platinum-olefin complex, and a platinum-vinyl siloxane complex are listed. The main constituent of the component 1a and that of the component 1b are the polysiloxane. Thus, in consideration of the compatibility between the polysiloxane and the catalysts, a platinum-vinyl siloxane complex is exemplary. For example, a solution of a vinyl methyl cyclic siloxane which is a platinum-vinyl-siloxane carbonyl cyclovinylmethylsiloxane complex, a solution of vinylpolydimethylsiloxane having the vinyl group at both terminals which is a platinum-divinyltetramethyldisiloxane complex, and a solution of cyclic methylvinylsiloxane which is a platinum-cyclovinylmethylsiloxane complex are listed.

It is exemplary that the concentration of the platinum in these solutions is 1 to 3 wt %. The mixing amount of the platinum group catalyst to be contained in the coating solution is 1 to 1,000 ppm, for example, 5 to 500 ppm, for example, 50 to 200 ppm for the polysiloxane of the component 1a in terms of the amount of the platinum. A reaction inhibitor having the function of suppressing the reaction between the component 1a and the component 1b may be added to the coating solution. As the reaction inhibitor, it is possible to use an addition reaction inhibitor for obtaining stability by appropriately inhibiting the hydroxylation between the vinyl group of the component 1a and the hydrogen group of the component 1b while the coating solution is in storage and while an operation is being performed. As the reaction inhibitor, 3-methyl-1-butyne-3-ol, 3-methyl-1-pentyne-3-ol, 3,5-dimethyl-1-hexyne-3-ol, 1-ethynylcyclohexanol, 3-methyl-3-trimethylsiloxane-1-butyne, 3-methyl-3-trimethylsiloxane-1-pentyne, 3-methyl-3-trimethylsiloxne-1-hexyne, 1-ethynyl-1-trimethylsiloxycyclohexane, bis(2,2-dimethyl-3-butynoxy)dimethylsilane, 1,3,5,7-tetraethyl-1,3,5,7-tetravinylcyclotetrasiloxane, and 1,1,3,3-tetramethyl-1,3-divinyldisiloxane are listed. The mixing amount of the reaction inhibitor to be contained in the coating solution can be 0.1 to 10 wt %, for example, 0.1 to 2 wt % for the polysiloxane of the component 1a.

The component 3 includes the auxiliary agent for enhancing the adhesion between the coating layer 3 and the core part 2 so that the coating layer 3 does not peel off the core part 2.

As the auxiliary agents of the component 3, cross-linkable alkoxysilanes such as alkyl alkoxysilane, phenylalkoxysilane, phenoxyalkoxysilane, alkylphenoxysilane, aminoalkylalkoxysilane, and glycidoxyalkylalkoxysilane are exemplary.

The alkyl alkoxysilane has at least one alkyl group having a carbon number of 1 to 20 and at least one alkoxy group having a carbon number of 1 to 4. As exemplary alkyl alkoxysilanes, it is possible to list methyltrimethoxysilane, methyltriethoxysilane, methyltriisobutoxysilane, methyltributoxysilane, methyl sec-trioctyloxysilane, isobutyltrimethoxysilane, cyclohexylmethyldimethoxysilane, diisopropyldimethoxysilane, propyltrimethoxysilane, diisobutyldimethoxysilane, n-octylmethoxysiloxane, ethyltrimethoxysilane, dimethyldimethoxysilane, octyltriethoxysilane, hexyltrimethoxysilane, hexyltriethoxysilane, octamethylcyclotetrasiloxane, methyltri(acryloyloxyethoxy)silane, octyltriethoxysilane, lauryltriethoxysilane, stearyltrimethoxtsilane, stearyltrimethoxtsilane, ethyltriethoxysilane, propyltriethoxysilane, butyltrimethoxysilane, butyltriethoxysilane, pentyltrimethoxysilane, pentyltriethoxysilane, heptyltrimethoxysilane, heptyltriethoxysilane, octyltrimethoxysilane, nonyltrimethoxysilane, nonyltriethoxysilane, decyltrimethoxysilane, decyltriethoxysilane, undecyltrimethoxysilane, undecyltriethoxysilane, dodecyltrimethoxysilane, dodecyltriethoxysilane, tridodecyltrimethoxysilane, tridodecyltriethoxysilane, tetradecyltrimethoxysilane, tetradecyltriethoxysilane, pentadecyltrimethoxysilane, pentadecyltriethoxysilane, hexadecyltrimethoxysilane, hexadecyltriethoxysilane, heptadecyltrimethoxysilane, heptadecyltriethoxysilane, octadecyltrimethoxysilane, octadecyltriethoxysilane, nonadecyltrimethoxysilane, nonadecyltriethoxysilane, eicosyltrimethoxysilane, and eicosyltriethoxysilane.

As the alkylphenoxysilane, for example, methyltriphenoxysilane is exemplary. As the phenoxyalkoxysilane, phenyltrimethoxysilane, phenyltriethoxysilane, diphenyldimethoxysilane, and diphenyldiethoxysilane are exemplary.

The mixing amount of the above-described auxiliary agents to be contained in the coating solution can be 0.1 to 10 wt %, for example, 0.1 to 5 wt % for the polysiloxane of the component 1a. For example, when the mixing amount of these auxiliary agents is less than 0.1 wt %, crosslinking is insufficiently performed, which makes it difficult for the coating layer 3 to adhere to the core part 2. For example, when the mixing amount thereof is more than 10 wt %, excessive crosslinking is performed, which deteriorates the flexibility and extensibility of the coating layer 3. For example, consequently, the follow-up performance of the coating layer 3 with the core part 2 is insufficient and thus the coating layer 3 has an insufficient adhesion to the core part 2.

As other exemplary auxiliary agents, alkoxysilane having an ureido group (—NH—CO—NH$_2$) and alkoxysilane having an uraren group (—NH—CO—NH—) are exemplified. As the alkoxysilane having the ureido group (—NH—CO—NH$_2$) and the alkoxysilane having the uraren group (—NH—CO—NH—), γ-ureidopropyltriethoxysilane, γ-ureidopropyldiethoxymethylsilane, methylurarenpropyldimethoxymethylsilane, 3-[(2-ureidoethyl)ureil]propyltrimethoxysilane, O=C[NHCH$_2$CH$_2$CH$_2$Si(OC$_2$H$_5$)$_3$]$_2$ are listed. The γ-ureidopropyltriethoxysilane is exemplary because it is satisfactory in its stability and easily commercially available. The mixing amount of the above-described auxiliary agents to be contained in the coating solution can be 1 to 10 wt %, for example, 3 to 10 wt % for the polysiloxane of the component 1a. For example, when the mixing amount of these auxiliary agents is less than 1 wt %, crosslinking is insufficiently performed, which makes it difficult for the coating layer 3 to adhere to the core part 2. For example, when the mixing amount thereof is more than 10 wt %, excessive crosslinking is performed, which deteriorates the flexibility and extensibility of the coating layer 3. For example, consequently, the follow-up performance of the coating layer 3 with the core part 2 is insufficient and thus the coating layer 3 has an insufficient adhesion to the core part 2.

As still other exemplary auxiliary agents, a product formed by a reaction between the alkoxysilane having an amino group and dicarboxylic anhydride is exemplary. The reaction product can be obtained by mixing the alkoxysilane having the amino group and the dicarboxylic anhydride with each other at a mixing ratio of the amino group to the carboxylic acid set to 0.5 to 2, for example, 0.8 to 1.2 in the mole rate, allowing both substances to react with each other in a solvent for several hours to tens and several hours at a room temperature to 90 degrees C., and distilling a solvent. As solvents to be used, alcohols such as methanol, ethanol, and isopropanol; and ketones such as acetone and methyl ethyl ketone are listed. It is exemplary to make the reaction between the above-described two substances while the solvent is refluxing. As the alkoxysilane having the amino group, 3-aminopropyltriethoxysilane, 3-(2-aminoethyl)aminopropyltrimethoxysilane, 3-(2-aminoethyl)aminopropylmethyldimethoxysilane, 3-aminopropyltrimethoxysilane, and 3-phenylaminopropyltrimethoxysilane are exemplary. As the dicarboxylic anhydride, phthalic anhydride, succinic anhydride, maleic anhydride, and glutaric anhydride are listed. The mixing amount of the above-described auxiliary agents to be contained in the coating solution can be 1 to 10 wt %, for example, 3 to 8 wt % for the polysiloxane of the component 1a. For example, when the mixing amount of these auxiliary agents is less than 1 wt %, crosslinking is insufficiently performed, which makes it difficult for the coating layer 3 to adhere to the core part 2. For example, when the mixing amount thereof is more than 10 wt %, excessive crosslinking is performed, which deteriorates the flexibility and extensibility of the coating layer 3. For example, consequently, the follow-up performance of the coating layer 3 with the core part 2 is insufficient and thus the coating layer 3 has an insufficient adhesion to the core part 2.

As still other exemplary auxiliary agents, glycidoxyalkylalkoxysilane may be used. As the glycidoxyalkylalkoxysilane, 3-glycidoxypropyltrimethoxysilane, 3-glycidoxypropyltriethoxysilane, 3-glycidoxypropylmethyldiethoxysilane, 3-glycidoxypropylmethyldimethoxysilane, and 2-(3,4-epoxycyclohexyl)ethyltrimethoxysilane are exemplary. The mixing amount of the above-described auxiliary agents of the component 3 to be contained in the coating solution can be 1 to 10 wt %, for example, 3 to 8 wt % for the polysiloxane of the component 1a. For example, when the mixing amount of these auxiliary agents is less than 1 wt %, crosslinking is insufficiently performed, which makes it difficult for the coating layer 3 to adhere to the core part 2. For example, when the mixing amount thereof is more than 10 wt %, excessive crosslinking is performed, which deteriorates the flexibility and extensibility of the coating layer 3. For example, consequently, the follow-up performance of the coating layer 3 with the core part 2 is insufficient and thus the coating layer 3 has an insufficient adhesion to the core part 2.

The syringe 10 has the above-described gasket 1, the outer cylinder 11 slidably accommodating the gasket 1 therein, and the plunger 17 which is mounted on the gasket 1 or can be mounted thereon.

A syringe is one example of the medical appliance. For example, as shown in FIG. 5, the syringe 10 is constructed of the outer cylinder 11, for use in the syringe, which has a needle-mounting portion 15 disposed at the distal part thereof and a pair of opposed flanges 16 disposed at the proximal end thereof; the gasket 1, for use in the syringe, which is capable of liquid-tightly and airtightly sliding on an inner surface 12 of the outer cylinder 11 for use in the syringe; the plunger 17 which is mounted on the gasket 1 for use in the syringe or can be mounted thereon; a sealing member 18 for sealing the needle-mounting portion 15 of the outer cylinder 11 for use in the syringe; and a medical agent accommodation portion 19, for accommodating a medical agent 26, which is formed among the sealing member 18, the inner surface 12 of the outer cylinder 11, and the gasket 1 for use in the syringe. Instead of the sealing member 18, a needle may be mounted on the needle-mounting portion 15. As shown in FIG. 5, the sealing member 18 may be of a type having a piercing portion into which a double ended needle can be directly inserted so that the medical agent can be administered by using the double ended needle or may be of a type in which the medical agent cannot be discharged until the sealing member is removed and the needle-mounting portion 15 is opened. The gasket 1 has the above-described coating layer 3 formed on its surface. In the syringe 10, it is exemplary that the dynamic sliding resistance value of the gasket 1 when the gasket 1 slides inside the outer cylinder 11 at a low speed (100 mm/minute) is not more than 20 N. Such a low dynamic sliding resistance value can be obtained by forming the above-described coating layer 3 on the surface of the gasket 1. It is exemplary that the dynamic sliding resistance value of the gasket 1 when the gasket 1 slides inside the outer cylinder 11 at the low speed (100 mm/minute) is 1 N to 20 N.

The syringe is a prefilled syringe 25 in which the medical agent is filled. It is exemplary that the prefilled syringe is composed of the syringe 10 and the medical agent 26, as shown in FIG. 5.

The syringe 10 has a construction similar to that of the above-described syringe in which the medical agent is not filled. The outer cylinder 11 for use in the syringe is a cylindrical member having the needle-mounting portion 15 disposed at the distal part thereof and the flange 16 disposed at the proximal end thereof. The outer cylinder 11 for use in the syringe is made of a material transparent or semitransparent. Because the syringe 10 is used for the prefilled syringe, it is exemplary that the outer cylinder 11 is made of a material having a low oxygen permeability or a low vapor permeability according to the kind of the medical agent to be filled therein. It is exemplary that the material forming the outer cylinder 11 has a glass transition point or a melting point not less than 110 degrees C.

As materials forming the outer cylinder 11, various general-purpose rigid plastic materials are exemplary. Polyolefins such as polypropylene, polyethylene, poly(4-methylpentene-1), and cyclic polyolefin; polyesters such as polyethylene terephthalate, polyethylene naphthalate, and non-crystalline polyarylate; polystyrene; polyamide; polycarbonate, polyvinyl chloride; acrylic resin; an acrylonitrile-butadiene-styrene copolymer, and non-crystalline polyetherimide are exemplary. The polypropylene, the poly(4-methylpentene-1), the cyclic polyolefin, the polyethylene naphthalate, and the non-crystalline polyetherimide are exemplary because these resins are transparent and resistant to heat sterilization. In addition to the outer cylinder, these resins can be used as materials to form containers capable of accommodating a medical agent. It is also possible to use glass as a material to form the outer cylinder.

As shown in FIG. 5, the plunger 17 has a sectionally cross-shaped body portion 20 extended axially; a plunger-side screwing portion 21, disposed at the distal part thereof, which screws on the plunger-mounting portion 4; a disk-shaped gasket-supporting portion disposed between the plunger-side screwing portion 21 and the body portion 20; a disk portion 22, for pressing use, which is disposed at the proximal end of the body portion 20; and a disk-shaped rib formed midway on the body portion 20.

The medical agent 26 is accommodated inside the syringe 10 of this embodiment. As the medical agent 26, it is possible to use both a liquid medicine and a solid agent such as a powdery medical agent and a freeze-dried medical agent. The liquid medicine, containing the surface active agent, which has a low viscosity and a high degree of penetration is exemplary because although the liquid medicine makes it difficult to allow the gasket to have sliding property and to be liquid-tight, the liquid medicine can be accommodated inside the syringe 10 which does not require silicone oil. In the case where the coating layer 3 is formed on the gasket 1 for the syringe at the part thereof which contacts the accommodated medical agent, it is possible to prevent the adsorption of the medical agent such as the liquid medicine which contains a component having a poor water solubility and has a high adsorbing property. Thus it is exemplary to use such a medical agent. As materials composing the plunger 17 and the sealing member 18, it is exemplary to use hard resins or semi-hard resins such as polyvinyl chloride, high-density polyethylene, polypropylene, polystyrene, polyethylene terephthalate, polycarbonate, acrylic resin, and the like. It is possible to use materials composing outer cylinders 11 not described herein.

The above-described syringe is one example of the medical appliance which moves in contact with the inner surface of the medical member. The medical appliance may be the appliance which moves in contact with the inner surface of the lumen. The medical appliance which moves in contact with the inner surface of the lumen includes a catheter, a guide wire, a blood vessel dilation appliance, and the like. The medical appliance may be appliances which move in contact with the inner surface of the medical member and that of the lumen. The medical appliance which moves in contact with the inner surface of the lumen includes the catheter, the guide wire, and the blood vessel dilation appliance which are inserted into the catheter (for example, a guiding catheter) which is a medical member such that the distal portions thereof are guided to an intended portion of the lumen.

An embodiment in which the medical appliance is applied to the guide wire is described below with reference to the drawing.

The guide wire of the embodiment shown in FIG. 6 has an inner core 52 composed of a body part 52a having a high rigidity and a distal part 52b, having a smaller diameter and a lower rigidity than the body part 52a, which is formed integrally with the body part 52a, a high radiographic visualization part 54 formed at the distal end of the inner core 52, and a sliding coating layer 53 enclosing the entire inner core 52 on which the high radiographic visualization part 54 is formed. As the sliding coating layer 53, a coating layer same as the above-described coating layer 3 is used.

The inner core 52 of the guide wire 50 has the body part 52a and the distal part 52b and is integrally formed of an elastic metal. The diameter of the distal part 52b is so formed as to be smaller than the distal end of the body part 52a. By so forming the distal part 52b as to have a small diameter, the distal part 52b has a lower rigidity than the body part. The diameter of the distal part 52b may be so set as to become gradually smaller toward the distal end thereof from the distal end of the body part 52a. By making the distal part of the inner core gradually smaller in its diameter, the distal part of the inner core gradually bends when a force is applied to the distal end of the body part 52a. Thus operability is improved.

It is exemplary that the inner core 52 is made of superelastic metals and stainless steels. As the superelastic metals, superelastic metallic bodies such as a TiNi alloy containing 49-58 atom % Ni, a Cu—Zn alloy containing 38.5 to 41.5 wt % Zn, a Cu—Zn—X alloy containing 1 to 10 wt % X (X=Be, Si, Al, Ga), and a Ni—Al alloy containing 36 to 38 atom % Al can be used. The TiNi alloy is exemplary.

In the embodiment shown in FIG. 6, the high radiographic visualization part 54 is a metallic annular member, having a high radiographic visualization performance, which is fixed to the distal end of the inner core 52. For example, the high radiographic visualization part 54 is formed of a pipe-shaped member or a coiled thin metallic wire having a high radiographic visualization. As metals having high radiographic visualization performance, gold, platinum, zinc, silver, bismuth, and tungsten are exemplary. Gold is exemplary.

As shown in FIG. 6, it is exemplary that the sliding coating layer 53 coating the entire inner core 52 including the distal part thereof has an almost uniform outer diameter. The sliding coating layer 53 has an almost uniform outer diameter to prevent the difference in level between the inner core 52 and the high radiographic visualization part 54 formed at the distal end of the inner core 52 from affecting the outer configuration of the guide wire 50.

A film made of the same material as that of the coating layer 3 described on the gasket of the above-described embodiment can be used as the sliding coating layer 53.

The outer diameter of the sliding coating layer is 0.25 to 1.04 mm, for example, 0.30 to 0.64 mm. The thickness of the sliding coating layer at the body part 52a of the inner core 52 is 0.25 to 1.04 mm, for example, 0.30 to 0.64 mm.

It is exemplary that the distal end (the distal end of the sliding coating layer 53) of the guide wire 50 has a curved surface, for example, a semispherical surface as shown in FIG. 6 to prevent a blood vessel wall from being damaged and improve the operability of the guide wire 50.

Although the entire inner core 52 of the guide wire 50 of this embodiment is coated with the sliding coating layer 53, the form of the inner core 52 is not limited to this one. The sliding coating layer 53 may be so constructed as to cover a part of the inner core 52. For example, the sliding coating layer 53 may be so constructed as to cover only the distal part of the inner core 52 or only the body part of the inner core 52.

EXAMPLES

Examples are described below.

The coating solution was prepared in accordance with methods used in the example 1 through 7 and the comparison examples 1 through 4.

Example 1

(Component 1a)

43 g of 1,5-diethenyl-3,3-bis[(ethenyldimethylsilyl)oxy]-1,1,5,5-tetramethylpentanetrisiloxane, 445 g of octamethylcyclotetrasiloxane, and 1.5 g of trifluoromethanesulfonic acid were measured and put into a 1 L egg-plant shaped flask and thereafter reacted with one another at 80 degrees C. for six hours while the components were being stirred. The temperature of the reactant was returned to a room temperature. Thereafter 1.2 g of calcium carbonate was added to the reactant. After the mixture was stirred for three hours, the calcium carbonate was removed therefrom by performing a filtering operation to complete polymerization. Thereafter stripping was performed for the reactant at 150 degrees C. for two hours under a reduced pressure (3 kPa). By performing the polymerization, polysiloxane having the branch structure was obtained. The viscosity of the obtained polysiloxane was 53 mPa·s. The content of the vinyl group was 2.2 wt %. The obtained product was used as the component 1a.

(Component 1b)

Polymethylhydrogensiloxane (content of the hydrogen group bonded to the silicon atom: 100 mol %, viscosity: 30 mPa·S, molecular weight: 2,100) having the trimethylsilyl group at both terminals thereof was used as the component 1b.

(Component 2)

10 wt % of ethinylcyclohexanol was mixed with polydimethylsiloxane (viscosity: 50 mPa·S, content of platinum: 3 wt %) which is a platinum-divinyltetramethyldisiloxane complex and has the vinyl group at both terminals thereof. The mixture was used as the component 2.

(Component 3)

Methyltriethoxysilane, γ-ureidopropyltriethoxysilane, and γ-glycidoxypropyltrimethoxysilane were used as the component 3.

(Coating Solution)

100 g of the component 1a, 7.4 g of the component 1b, 0.33 g of the component 2, 1 g of the methyltriethoxysilane of the component 3, 1 g of the γ-ureidopropyltriethoxysilane, and 5 g of the γ-glycidoxypropyltrimethoxysilane were mixed with one another to prepare a coating solution. The viscosity (25 degrees C.) of the obtained coating solution was 46 mPa·s.

Example 2

(Component 1a)

22 g of the 1,5-diethenyl-3,3-bis[(ethenyldimethylsilyl)oxy]-1,1,5,5-tetramethylpentanetrisiloxane, 593 g of the octamethylcyclotetrasiloxane, and 1.5 g of the trifluoromethanesulfonic acid were measured and put into the 1 L egg-plant shaped flask and thereafter reacted with one another at 80 degrees C. for six hours while the components were being stirred. The temperature of the reactant was returned to the room temperature. Thereafter 1.2 g of calcium carbonate was added to the reactant. After the mixture was stirred for three hours, the calcium carbonate was removed therefrom by performing the filtering operation to complete polymerization. Thereafter stripping was performed for the reactant at 150 degrees C. for two hours under the reduced pressure (3 kPa). By performing the polymerization, the polysiloxane having the branch structure was obtained. The viscosity of the obtained polysiloxane was 168 mPa·s. The content of the vinyl group was 0.9 wt %. The obtained product was used as the component 1a.

(Component 1b)

A methylhydrogen siloxane-dimethylsiloxane copolymer (content of the hydrogen group bonded to the silicon atom: 30 mol %, viscosity: 35 mPa·S, molecular weight: 2,000) having the trimethylsilyl group at both terminals thereof was used as the component 1b.

(Component 2)

10 wt % of the ethinylcyclohexanol was mixed with the polydimethylsiloxane (viscosity: 50 mPa·S, content of platinum: 3 wt %) which is the platinum-divinyltetramethyldisiloxane complex and has the vinyl group at both terminals thereof. The mixture was used as the component 2.

(Component 3)

140 g of γ-aminopropyltriethoxysilane was dripped to a solution in which 62 g of maleic anhydride was dissolved in 200 g of ethanol at a room temperature. Thereafter the above-described components were reacted at 80 degrees C. for 15 hours with the ethanol refluxing. The obtained reactant, phenyltriethoxysilane and γ-glycidoxypropyltrimethoxysilane were used as the component 3.

(Coating Solution)

100 g of the component 1a, 9.7 g of the component 1b, 0.67 g of the component 2, 1 g of the phenyltriethoxysilane of the component 3, 5 g of the above-described reactants, and 1 g of the γ-glycidoxypropyltrimethoxysilane were mixed with one another to prepare a coating solution. The viscosity (25 degrees C.) of the coating solution was 143 mPa·s.

Example 3

(Component 1a)

43 g of the 1,5-diethenyl-3,3-bis[(ethenyldimethylsilyl)oxy]-1,1,5,5-tetramethylpentanetrisiloxane, 18 g of 1,3,5,7-tetravinyltetramethylcyclotetrasiloxane, 445 g of the octamethylcyclotetrasiloxane, and 1.5 g of the trifluoromethanesulfonic acid were measured and put into the 1 L egg-plant shaped flask and thereafter reacted with one another at 80 degrees C. for six hours while the components were being stirred. The temperature of the reactant was returned to the room temperature. Thereafter 1.2 g of the calcium carbonate was added to the reactant. After the mixture was stirred for three hours, the calcium carbonate was removed therefrom by performing the filtering operation to complete polymerization. Thereafter the stripping was performed for the reactant at 150 degrees C. for two hours under the reduced pressure (3 kPa). By performing the polymerization, the polysiloxane having the branch structure was obtained. The viscosity of the obtained polysiloxane was 136 mPa·s. The content of the vinyl group was 3.2 wt %. The obtained product was used as the component 1a.

(Component 1b)

The polymethylhydrogensiloxane (content of the hydrogen group bonded to the silicon atom: 100 mol %, viscosity: 30 mPa·S, molecular weight: 2,100) having the trimethylsilyl group at both terminals thereof was used as the component 1b.

(Component 2)

10 wt % of the ethinylcyclohexanol was mixed with the polydimethylsiloxane (viscosity: 50 mPa·S, content of platinum: 3 wt %) which is the platinum-divinyltetramethyldisiloxane complex and has the vinyl group at both terminals thereof. The mixture was used as the component 2.
(Component 3)

The methyltriethoxysilane, the γ-ureidopropyltriethoxysilane, and the γ-glycidoxypropyltrimethoxysilane were used as the component 3.
(Coating Solution)

100 g of the component 1a, 10.7 g of the component 1b, 0.33 g of the component 2, 1 g of the methyltriethoxysilane of the component 3, 5 g of the γ-ureidopropyltriethoxysilane, and 3 g of the γ-glycidoxypropyltrimethoxysilane were mixed with one another to prepare a coating solution. The viscosity (25 degrees C.) of the obtained coating solution was 122 mPa·s.

Example 4

(Component 1a)

22 g of 1,5-diethenyl-3,3-bis[(ethenyldimethylsilyl)oxy]-1,1,5,5-tetramethylpentanetrisiloxane, 88 g of the 1,3,5,7-tetravinyltetramethylcyclotetrasiloxane, 445 g of the octamethylcyclotetrasiloxane, and 1.5 g of the trifluoromethanesulfonic acid were measured and put into the 1 L egg-plant shaped flask and thereafter reacted with one another at 80 degrees C. for six hours while the components were being stirred. The temperature of the reactant was returned to the room temperature. Thereafter, 1.2 g of the calcium carbonate was added to the reactant. After the mixture was stirred for three hours, the calcium carbonate was removed therefrom by performing the filtering operation to complete polymerization. Thereafter, the stripping was performed for the reactant at 150 degrees C. for two hours under the reduced pressure (3 kPa). By performing the polymerization, the polysiloxane having the branch structure was obtained. The viscosity of the obtained polysiloxane was 108 mPa·s. The content of the vinyl group was 5.8 wt %. The obtained product was used as the component 1a.
(Component 1b)

The polymethylhydrogensiloxane (content of the hydrogen group bonded to the silicon atom: 100 mol %, viscosity: 30 mPa·S, molecular weight: 2,100) having the trimethylsilyl group at both terminals thereof was used as the component 1b.
(Component 2)

10 wt % of the ethinylcyclohexanol was mixed with the polydimethylsiloxane (viscosity: 50 mPa·S, content of platinum: 3 wt %) which is the platinum-divinyltetramethyldisiloxane complex and has the vinyl group at both terminals thereof. The mixture was used as the component 2.
(Component 3)

140 g of the γ-aminopropyltriethoxysilane was dripped to the solution in which 62 g of the maleic anhydride was dissolved in 200 g of the ethanol at the room temperature. Thereafter, the above-described components were reacted at 80 degrees C. for 15 hours with the ethanol refluxing. The obtained reactant, the methyltriethoxysilane, and the γ-glycidoxypropyltrimethoxysilane were used as the component 3.
(Coating Solution)

100 g of the component 1a, 19.5 g of the component 1b, 0.33 g of the component 2, 1 g of the methyltriethoxysilane of the component 3, 1 g of the above-described reactant, and 5 g of the γ-glycidoxypropyltrimethoxysilane were mixed with one another to prepare a coating solution. The viscosity (25 degrees C.) of the coating solution was 91 mPa·s.

Example 5

(Component 1a)

11 g of the 1,5-diethenyl-3,3-bis[(ethenyldimethylsilyl)oxy]-1,1,5,5-tetramethylpentanetrisiloxane, 88 g of the 1,3,5,7-tetravinyltetramethylcyclotetrasiloxane, 371 g of the octamethylcyclotetrasiloxane, and 1.5 g of the trifluoromethanesulfonic acid were measured and put into the 1 L egg-plant shaped flask and thereafter reacted with one another at 80 degrees C. for six hours while the components were being stirred. The temperature of the reactant was returned to the room temperature. Thereafter, 1.2 g of the calcium carbonate was added to the reactant. After the mixture was stirred for three hours, the calcium carbonate was removed therefrom by performing the filtering operation to complete polymerization. Thereafter, the stripping was performed for the reactant at 150 degrees C. for two hours under the reduced pressure (3 kPa). By performing the polymerization, the polysiloxane having the branch structure was obtained. The viscosity of the obtained polysiloxane was 460 mPa·s. The content of the vinyl group was 6.3 wt %. The obtained product was used as the component 1a.
(Component 1b)

The methylhydrogen siloxane-dimethylsiloxane copolymer (content of the hydrogen group bonded to the silicon atom: 30 mol %, viscosity: 35 mPa·S, molecular weight: 2,000) having the trimethylsilyl group at both terminals thereof was used as the component 1b.
(Component 2)

10 wt % of the ethinylcyclohexanol was mixed with the polydimethylsiloxane (viscosity: 50 mPa·S, content of platinum: 3 wt %) which is the platinum-divinyltetramethyldisiloxane complex and has the vinyl group at both terminals thereof. The mixture was used as the component 2.
(Component 3)

The phenyltriethoxysilane, the γ-ureidopropyltriethoxysilane, and the γ-glycidoxypropyltrimethoxysilane were used as the component 3.
(Coating Solution)

100 g of the component 1a, 70.2 g of the component 1b, 0.67 g of the component 2, 1 g of the phenyltriethoxysilane of the component 3, 5 g of the γ-ureidopropyltriethoxysilane, and 3 g of the γ-glycidoxypropyltrimethoxysilane were mixed with one another to prepare a coating solution. The viscosity (25 degrees C.) of the obtained coating solution was 422 mPa·s.

Example 6

(Component 1a)

18 g of the 1,3,5,7-tetravinyltetramethylcyclotetrasiloxane, 445 g of the octamethylcyclotetrasiloxane, and 1.5 g of the trifluoromethanesulfonic acid were measured and put into the 1 L egg-plant shaped flask and thereafter reacted with one another at 80 degrees C. for six hours while the components were being stirred. The temperature of the reactant was returned to the room temperature. Thereafter, 1.2 g of the calcium carbonate was added to the reactant. After the mixture was stirred for three hours, the calcium carbonate was removed therefrom by performing the filtering operation to complete polymerization. Thereafter, the stripping was performed for the reactant at 150 degrees C. for two hours under the reduced pressure (3 kPa). By performing the polymerization, the polysiloxane having the branch structure was obtained. The viscosity of the obtained polysiloxane was 641 mPa·s. The content of the vinyl group was 5.4 wt %. The mixture of 10 g of the obtained product and 90 g of the obtained product of the polysiloxane of the example 1 having the branch structure was used as the component 1a.

(Component 1b)

The methylhydrogen siloxane-dimethylsiloxane copolymer (content of the hydrogen group bonded to the silicon atom: 30 mol %, viscosity: 35 mPa·S, molecular weight: 2,000) having the trimethylsilyl group at both terminals thereof was used as the component 1b.

(Component 2)

10 wt % of ethinylcyclohexanol was mixed with the polydimethylsiloxane (viscosity: 50 mPa·S, content of platinum: 3 wt %) which is the platinum-divinyltetramethyldisiloxane complex and has the vinyl group at both terminals thereof. The mixture was used as the component 2.

(Component 3)

140 g of the γ-aminopropyltriethoxysilane was dripped to the solution in which 62 g of the maleic anhydride was dissolved in 200 g of the ethanol at the room temperature. Thereafter the above-described components were reacted at 80 degrees C. for 15 hours with the ethanol refluxing. The obtained reactant, the phenyltriethoxysilane, and the γ-glycidoxypropyltrimethoxysilane were used as the component 3.

(Coating Solution)

100 g of the component 1a, 23.4 g of the component 1b, 0.33 g of the component 2, 1 g of the phenyltriethoxysilane of the component 3, 5 g of the above-described reactant, and 5 g of the γ-glycidoxypropyltrimethoxysilane were mixed with one another to prepare a coating solution. The viscosity (25 degrees C.) of the coating solution was 86 mPa·s.

Example 7

(Component 1a)

20 g of the mixture of polydimethylsiloxane (content of vinyl group: 0.04 wt %, viscosity: 1,860 mPa) having the straight-chain structure and the vinyl group at both terminals thereof and 80 g of the obtained product of the example 3 was used as the component 1a.

(Component 1b)

The polymethylhydrogensiloxane (content of the hydrogen group bonded to the silicon atom: 100 mol %, viscosity: 30 mPa·S, molecular weight: 2,100) having the trimethylsilyl group at both terminals thereof was used as the component 1b.

(Component 2)

10 wt % of the ethinylcyclohexanol was mixed with the polydimethylsiloxane (viscosity: 50 mPa·S, content of platinum: 3 wt %) which is the platinum-divinyltetramethyldisiloxane complex and has the vinyl group at both terminals thereof. The mixture was used as the component 2.

(Component 3)

The methyltriethoxysilane, the γ-ureidopropyltriethoxysilane, and the γ-glycidoxypropyltrimethoxysilane were used as the component 3.

(Coating Solution)

100 g of the component 1a, 44.8 g of the component 1b, 0.33 g of the component 2, 1 g of the methyltriethoxysilane of the component 3, 1 g of the γ-ureidopropyltriethoxysilane, and 5 g of the γ-glycidoxypropyltrimethoxysilane were mixed with one another to prepare a coating solution. The viscosity (25 degrees C.) of the obtained coating solution was 457 mPa·s.

Comparison Example 1

(Component 1a)

18 g of the 1,3,5,7-tetravinyltetramethylcyclotetrasiloxane, 445 g of the octamethylcyclotetrasiloxane, and 1.5 g of the trifluoromethanesulfonic acid were measured and put into the 1 L egg-plant shaped flask and thereafter reacted with one another at 80 degrees C. for six hours while the components were being stirred. The temperature of the reactant was returned to the room temperature. Thereafter 1.2 g of the calcium carbonate was added to the reactant. After the mixture was stirred for three hours, the calcium carbonate was removed therefrom by performing the filtering operation to complete polymerization. Thereafter the stripping was performed for the reactant at 150 degrees C. for two hours under the reduced pressure (3 kPa). By performing the polymerization, the polysiloxane having the straight-chain structure was obtained. The viscosity of the obtained polysiloxane having the straight-chain structure was 641 mPa·s. The content of the vinyl group was 1.2 wt %. The obtained product was used as the component 1a.

(Component 1b)

The methylhydrogen siloxane-dimethylsiloxane copolymer (content of the hydrogen group bonded to the silicon atom: 30 mol %, viscosity: 35 mPa·S, molecular weight: 2,000) having the trimethylsilyl group at both terminals thereof was used as the component 1b.

(Component 2)

10 wt % of the ethinylcyclohexanol was mixed with the polydimethylsiloxane (viscosity: 50 mPa·S, content of platinum: 3 wt %) which is the platinum-divinyltetramethyldisiloxane complex and has the vinyl group at both terminals thereof. The mixture was used as the component 2.

(Component 3)

140 g of the γ-aminopropyltriethoxysilane was dripped to the solution in which 62 g of the maleic anhydride was dissolved in 200 g of the ethanol at the room temperature. Thereafter the above-described substances were reacted at 80 degrees C. for 15 hours with the ethanol refluxing. The obtained reactant, the phenyltriethoxysilane and the γ-glycidoxypropyltrimethoxysilane were used as the component 3.

(Coating Solution)

100 g of the component 1a, 12.9 g of the component 1b, 0.33 g of the component 2, 1 g of the phenyltriethoxysilane of the component 3, 1 g of the above-described reactant, and 5 g of the γ-glycidoxypropyltrimethoxysilane were mixed with one another to prepare a coating solution. The viscosity (25 degrees C.) of the coating solution was 608 mPa·s.

Comparison Example 2

(Component 1a)

9 g of the 1,3,5,7-tetravinyltetramethylcyclotetrasiloxane, 445 g of the octamethylcyclotetrasiloxane, and 1.5 g of the trifluoromethanesulfonic acid were measured and put into the 1 L egg-plant shaped flask and thereafter reacted with one another at 80 degrees C. for six hours while the components were being stirred. The temperature of the reactant was returned to the room temperature. Thereafter, 1.2 g of the calcium carbonate was added to the reactant. After the mixture was stirred for three hours, the calcium carbonate was removed therefrom by performing the filtering operation to complete polymerization. Thereafter, the stripping was performed for the reactant at 150 degrees C. for two hours under the reduced pressure (3 kPa). By performing the polymerization, the polysiloxane having the straight-chain structure was obtained. The viscosity of the obtained polysiloxane having the straight-chain structure was 887 mPa·s. The content of the vinyl group was 0.6 wt %. The obtained product was used as the component 1a.

(Component 1b)

The polymethylhydrogensiloxane (content of the hydrogen group bonded to the silicon atom: 100 mol %, viscosity:

30 mPa·S, molecular weight: 2,100) having the trimethylsilyl group at both terminals thereof was used as the component 1b.
(Component 2)
10 wt % of the ethinylcyclohexanol was mixed with the polydimethylsiloxane (viscosity: 50 mPa·S, content of platinum: 3 wt %) which is the platinum-divinyltetramethyldisiloxane complex and has the vinyl group at both terminals thereof. The mixture was used as the component 2.
(Component 3)
The methyltriethoxysilane, the γ-ureidopropyltriethoxysilane, and the γ-glycidoxypropyltrimethoxysilane were used as the component 3.
(Coating Solution)
100 g of the component 1a, 2 g of the component 1b, 0.67 g of the component 2, 1 g of the methyltriethoxysilane of the component 3, 5 g of the γ-ureidopropyltriethoxysilane, and 3 g of the γ-glycidoxypropyltrimethoxysilane were mixed with one another to prepare a coating solution. The viscosity (25 degrees C.) of the coating solution was 857 mPa·s.

Comparison Example 3

(Component 1a)
The polydimethylsiloxane (content of vinyl group: 0.4 wt %, viscosity: 500 mPa) having the straight-chain structure and the vinyl group at both terminals thereof was used as the component 1a.
(Component 1b)
The polymethylhydrogensiloxane (content of the hydrogen group bonded to the silicon atom: 100 mol %, viscosity: 30 mPa·S, molecular weight: 2,100) having the trimethylsilyl group at both terminals thereof was used as the component 1b.
(Component 2)
10 wt % of the ethinylcyclohexanol was mixed with the polydimethylsiloxane (viscosity: 50 mPa·S, content of platinum: 3 wt %) which is the platinum-divinyltetramethyldisiloxane complex and has the vinyl group at both terminals thereof. The mixture was used as the component 2.
(Component 3)
140 g of the γ-aminopropyltriethoxysilane was dripped to the solution in which 62 g of the maleic anhydride was dissolved in 200 g of the ethanol at the room temperature. Thereafter the above-described components were reacted at 80 degrees C. for 15 hours with the ethanol refluxing. The obtained reactant, the methyltriethoxysilane, and the γ-glycidoxypropyltrimethoxysilane were used as the component 3.
(Coating Solution)
100 g of the component 1a, 1.3 g of the component 1b, 0.67 g of the component 2, 1 g of the methyltriethoxysilane of the component 3, 5 g of the above-described reactant, and 5 g of the γ-glycidoxypropyltrimethoxysilane were mixed with one another to prepare a coating solution. The viscosity (25 degrees C.) of the obtained coating solution was 468 mPa·s.

Comparison Example 4

(Component 1a)
The polydimethylsiloxane (content of vinyl group: 0.4 wt %, viscosity: 1,860 mPa) having the straight-chain structure and the vinyl group at both terminals thereof was used as the component 1a.
(Component 1b)
The methylhydrogen siloxane-dimethylsiloxane copolymer (content of the hydrogen group bonded to the silicon atom: 30 mol %, viscosity: 35 mPa·S, molecular weight: 2,000) having the trimethylsilyl group at both terminals thereof was used as the component 1b.

(Component 2)
10 wt % of the ethinylcyclohexanol was mixed with the polydimethylsiloxane (viscosity: 50 mPa·S, content of platinum: 3 wt %) which is the platinum-divinyltetramethyldisiloxane complex and has the vinyl group at both terminals thereof. The mixture was used as the component 2.
(Component 3)
The phenyltriethoxysilane, the γ-ureidopropyltriethoxysilane, and the γ-glycidoxypropyltrimethoxysilane were used as the component 3.
(Coating Solution)
100 g of the component 1a, 0.4 g of the component 1b, 0.33 g of the component 2, 1 g of the phenyltriethoxysilane of the component 3, 5 g of the γ-ureidopropyltriethoxysilane, and 5 g of the γ-glycidoxypropyltrimethoxysilane were mixed with one another to prepare a coating solution. The viscosity (25 degrees C.) of the coating solution was 1,829 mPa·s.

By using butyl rubber, the core parts of the gaskets for syringes having a configuration shown in FIGS. 1 and 2 were prepared. The core parts were formed by press molding a vulcanized rubber composition containing the butyl rubber and an additive added thereto. Regarding the configuration of the obtained core parts, the length was 20 mm. The outer diameter at the distal-side and proximal-side annular ribs was 30 mm. The distance between the center of the distal-side annular rib and the center of the proximal-side annular rib was 10 mm. The outer diameter at a portion where the distal-side annular rib and the proximal-side annular rib have an equal outer diameter was 27 mm. The length (depth) of the plunger-mounting concave portion having a female screw at its inner side was 10 mm. The inner diameter of the plunger-mounting concave portion at its distal side was 18 mm. The inner diameter of the plunger-mounting concave portion at its proximal side was 21 mm.

After the core members of the gaskets were heat-treated at 90 degrees C. for 30 minutes in an environment having a room temperature and a normal pressure, the core members were rotated (300 rpm) about the axes thereof. Coating solutions of examples 1 through 7 and comparison examples 1 through 4 were applied to the side surface of each of the gaskets as sprays while the gaskets were rotating. Thereafter the coating solutions were dried at 150 degrees C. for 30 minutes. In this manner, the gaskets were produced. The average thickness of the coating layer formed on the surface of each core member is as shown in table 1.

TABLE 1

|  | Average thickness of coating layer |
| --- | --- |
| Example 1 | about 10 μm |
| Example 2 | about 15 μm |
| Example 3 | about 15 μm |
| Example 4 | about 10 μm |
| Example 5 | about 20 μm |
| Example 6 | about 10 μm |
| Example 7 | about 25 μm |
| Comparison Example 1 | about 50 μm |
| Comparison Example 2 | about 80 μm |
| Comparison Example 3 | about 25 μm |
| Comparison Example 4 | about 190 μm |

(Experiment 1: Sliding Resistance Measurement Test)
Polypropylene (produced by Japan Polychem Corporation) used as a material forming outer cylinders for syringes was injection-molded to form the outer cylinders for the syringes each having the configuration shown in FIG. 5. The cylindrical portion of each of the outer cylinders for the syringes had an inner diameter of 29 mm and a length of 121 mm. The polypropylene (produced by Japan Polychem Corporation) used as a material of plungers was injection-molded to form the plungers each having the configuration shown in FIG. 5.

The above-described outer cylinders for the syringes, the gaskets of the examples 1 through 7 and the comparison examples 1 through 4, and the above-described plungers were assembled to form the syringes.

The sliding resistance value of each syringe was measured by using an autograph (model name: EZ-Test manufactured by Shimazu Seisakusho Co., Ltd.). More specifically, with the distal end of each syringe and the proximal end of the plunger being fixed to a fixing portion of the autograph to which an object to be measured was fixed, the plungers were moved downward 60 mm at a speed of 100 mm/minute to measure the initial sliding resistance value and maximum sliding resistance value (N) of each syringe. Table 2 shows the results.

TABLE 2

| | Sliding resistance value (N) | | Pressure test | High-penetration liquid sealing performance test | Remarks |
|---|---|---|---|---|---|
| | Initial | Maximum | | | |
| Example 1 | 4.8 | 6.8 | Passed | Passed | — |
| Example 2 | 5.5 | 7.0 | Passed | Passed | — |
| Example 3 | 5.3 | 7.1 | Passed | Passed | — |
| Example 4 | 5.1 | 7.2 | Passed | Passed | — |
| Example 5 | 5.9 | 6.9 | Passed | Passed | — |
| Example 6 | 5.2 | 7.1 | Passed | Passed | — |
| Example 7 | 6.2 | 7.3 | Passed | Passed | — |
| Comparison Example 1 | 15.4 | 18.2 | Passed | Passed | — |
| Comparison example 2 | 24.1 | 26.7 | Passed | Passed | — |
| Comparison example 3 | — | — | — | — | coating layers destroyed |
| Comparison example 4 | — | — | — | — | coating layers destroyed |

As shown in table 2, the syringes using the gaskets of the examples 1 through 7 and the comparison examples 1 and 2 had almost equal initial and maximum sliding resistance values. In addition, each of the syringes had a small difference between the initial sliding resistance value and maximum sliding resistance value thereof. There is little fear that more than a predetermined amount of a liquid medicine was discharged from the syringes when the plungers were started to be pressed. Therefore, the syringes were capable of discharging the liquid medicine safely and accurately. Favorable results that the initial and maximum sliding resistance values were not more than 10N were obtained. But in the syringes using the gaskets of the comparison examples 1 and 2, the coating layers were destroyed and thus the sliding resistance values could not be measured.

The above-described outer cylinders for the syringes, the gaskets of the example 1 through 7 and the comparison example 1, and the above-described plungers were assembled to form the syringes. Thereafter, 40 ml of purified water was injected to each syringe barrel. After a sealing member was fitted on the distal end of each syringe barrel to seal it, autoclave sterilization was performed. Thereafter, the sliding resistance value of each syringe was measured by the autograph (model name: EZ-Test, manufactured by Shimazu Seisakusho Co., Ltd.) in the above-described manner. The initial sliding resistance value of each syringe and the maximum sliding resistance value (N) thereof were measured at a test speed of 20 to 500 mm/minute. Table 3 shows the results.

TABLE 3

| | Maximum sliding resistance value (N) | | | |
|---|---|---|---|---|
| | 20 mm/min | 50 mm/min | 100 mm/min | 50 mm/min |
| Example 1 | 9.2 | 11.0 | 14.7 | 29.0 |
| Example 2 | 9.6 | 10.9 | 15.1 | 26.5 |
| Example 3 | 9.1 | 11.2 | 14.6 | 25.9 |
| Example 4 | 9.3 | 11.7 | 15.2 | 27.7 |
| Example 5 | 9.2 | 11.0 | 14.9 | 28.9 |
| Example 6 | 9.5 | 11.3 | 15.0 | 28.1 |
| Example 7 | 9.9 | 12.5 | 15.4 | 29.6 |
| Comparison example 1 | 26.3 | 31.1 | 43.8 | 59.6 |
| Comparison example 2 | 37.9 | 49.7 | 63.1 | 88.2 |

As shown in Table 3, it has been found that the syringes using the gaskets of the example 1 through 7 had low sliding resistance values at a test speed lower than 100 mm/minute. Thus, it has been found that at a speed suitable for injecting the medical agent into a vein, the syringes using the gaskets of the example 1 through 7 had preferable sliding performance.

The number of samples used in each test was 10. The numerical values in the tables show the average of the values of the 10 samples.

By using glass (produced by Shiotani Glass Co., Ltd.) as a material of outer cylinders for syringes, the outer cylinders for the syringes having the configuration shown in FIG. 5 were formed. The cylindrical portion of each of the outer cylinders for the syringes had an inner diameter of 23 mm and a length of 76 mm. The polypropylene (produced by Japan Polychem Corporation) used as a material forming plungers was injection-molded to form the plungers each having the configuration shown in FIG. 5.

The above-described outer cylinders for syringes, the gaskets of the example 1 through 7 and the comparison examples 1 and 2, and the above-described plungers were assembled to form syringes. Thereafter, 20 ml of purified water was injected to the outer cylinders. Thereafter, sliding resistance values were measured by the autograph (model name: EZ-Test, manufactured by Shimazu Seisakusho Co., Ltd.) in the above-described manner. More specifically, with the distal end of each syringe and the proximal end of each plunger being fixed to the fixing portion of the autograph to which an object to be measured was fixed, each plunger was moved downward 45 mm at speeds of 20, 50, 100, and 500 mm/minute to measure the maximum sliding resistance value (N). Table 4 shows the results.

TABLE 4

| | Maximum sliding resistance value (N) | | | |
|---|---|---|---|---|
| | 20 mm/min | 50 mm/min | 100 mm/min | 500 mm/min |
| Example 1 | 6.1 | 7.3 | 11.2 | 14.3 |
| Example 2 | 6.3 | 7.1 | 11.5 | 14.2 |
| Example 3 | 6.2 | 7.1 | 11.7 | 14.1 |
| Example 4 | 6.1 | 7.2 | 11.3 | 14.6 |
| Example 5 | 6.3 | 7.0 | 11.1 | 14.2 |
| Example 6 | 6.5 | 7.6 | 11.9 | 14.9 |
| Example 7 | 6.8 | 7.9 | 12.4 | 15.0 |
| Comparison example 1 | 19.2 | 26.7 | 38.8 | 48.8 |

TABLE 4-continued

|  | Maximum sliding resistance value (N) | | | |
| --- | --- | --- | --- | --- |
|  | 20 mm/min | 50 mm/min | 100 mm/min | 500 mm/min |
| Comparison example 2 | 27.4 | 40.1 | 52.9 | 69.9 |

(Experiment 2: Pressure Test Specified in Standard of Sterilized Syringe Barrel)

The polypropylene (produced by Japan Polychem Corporation) used as a material forming outer cylinders for syringes was injection-molded to form the outer cylinders for the syringes each having the configuration shown in FIG. 5. The cylindrical portion of each of the outer cylinders for the syringes had an inner diameter of 29 mm and a length of 121 mm. The polypropylene (produced by Japan Polychem Corporation) used as a material of plungers was injection-molded to form the plungers each having the configuration shown in FIG. 5.

The above-described outer cylinders for the syringes, the gaskets of the examples 1 through 7 and the comparison examples 1 and 2, and the above-described plungers were assembled to form the syringes.

A test was conducted in accordance with the pressure test specified in the standard of the sterilized plastic syringe barrel which can be immediately used as it is and should be disposed after using it one time (notified on Dec. 11, 1998 by Director of Pharmaceutical and Medical Safety Bureau in No. 1079 issue of Pharmaceutical Development). Table 2 shows the results.

The number of samples used in the test was five. "Passed" was marked for samples of the examples and the comparison example in which all of the five samples passed inspection.

(Experiment 3: Test for Examining Sealing Performance of High-Penetration Liquid)

The polypropylene (produced by Japan Polychem Corporation) used as a material forming outer cylinders for syringes was injection-molded to form the outer cylinders for the syringes each having the configuration shown in FIG. 5. The cylindrical portion of each of the outer cylinders for the syringes had an inner diameter of 29 mm and a length of 121 mm. The polypropylene (produced by Japan Polychem Corporation) used as a material of plungers was injection-molded to form the plungers each having the configuration shown in FIG. 5.

The above-described outer cylinders for the syringes, the gaskets of the examples 1 through 7 and the comparison examples 1 and 2, and the above-described plungers were assembled to form the syringes.

Thereafter, by using an "Ageless" (registered trademark in Japan) "Checker" (produced by Mitsubishi Gas Chemical Company) for use in a test for examining the sealing performance of a heat sealing portion made of a soft plastic packing material, a sealing performance test (the distal end of the syringe was sealed in the length of 40 ml by fitting the sealing member on the distal end thereof) was conducted. The syringes were left overnight to visually observe liquid leak from the sliding portion of each gasket. Table 2 shows the results.

The number of samples used in the test was five. "Passed" was marked for the samples of the examples and the comparison example in which all of the five samples passed inspection.

(Experiment 4: Fixing Test)

The polypropylene (produced by Japan Polychem Corporation) used as a material forming outer cylinders for syringes was injection-molded to form the outer cylinders for the syringes each having the configuration shown in FIG. 5. The cylindrical portion of each of the outer cylinders for the syringes had an inner diameter of 29 mm and a length of 121 mm. The polypropylene (produced by Japan Polychem Corporation) used as a material of plungers was injection-molded to form the plungers each having the configuration shown in FIG. 5.

The above-described outer cylinders for the syringes, the gaskets of the examples 1,4, and 5 and the comparison example 1, and the above-described plungers were assembled to form syringes. Thereafter the syringes were allowed to stand one day in a constant-temperature bath having temperatures of 40 degrees C., 60 degrees C., and 80 degrees C. and thereafter 10 days, 20 days, and 30 days in the constant-temperature bath having a temperature of 60 degrees C. To evaluate the fixing degree of each gasket to the outer cylinder for the syringe, the initial sliding resistance value of each syringe was measured by the autograph (model name: EZ-Test, manufactured by Shimazu Seisakusho Co., Ltd.). More specifically, with the distal end of each syringe and the proximal end of each plunger being fixed to the fixing portion of the autograph to which an object to be measured was fixed, the plungers were moved downward 60 mm at a speed of 100 mm/minute to measure the initial sliding resistance value (N) of each syringe. Table 5 shows the results.

TABLE 5

| | Initial sliding resistance value (N) | | | | | | |
| --- | --- | --- | --- | --- | --- | --- | --- |
| | Initial | 40 degrees C. | 60 degrees C. | 80 degrees C. | 60 degrees C. | | |
| | time point in test | grees C. | grees C. one day | grees C. | 10 days | 20 days | 30 days |
| Example 1 | 4.8 | 5.2 | 5.8 | 7.2 | 7.5 | 8.0 | 8.9 |
| Example 4 | 5.1 | 5.5 | 6.1 | 6.9 | 7.0 | 7.8 | 9.1 |
| Example 5 | 5.9 | 6.1 | 6.3 | 7.4 | 7.4 | 8.2 | 9.1 |
| Comparison example 1 | 15.4 | 16.8 | 17.4 | 18.1 | 18.6 | 23.7 | 28.9 |

(Experiment 5: Test for Examining Insoluble Fine Particles)

The polypropylene (produced by Japan Polychem Corporation) used as a material forming outer cylinders for syringes was injection-molded to form the outer cylinders for the syringes each having the configuration shown in FIG. 5. The cylindrical portion of each of the outer cylinders for the syringes had an inner diameter of 29 mm and a length of 121 mm. The polypropylene (produced by Japan Polychem Corporation) used as a material forming plungers was injection-molded to form the plungers each having the configuration shown in FIG. 5. The above-described outer cylinders for the syringes, the gaskets of the examples 1, 4, and 5 and the comparison example 1, and the above-described plungers were assembled to form syringes.

Thereafter, 40 ml of purified water was injected to each syringe barrel. After the sealing member was fitted on the distal end of the syringe barrel to seal it, autoclave sterilization was performed to produce prefilled syringes. Thereafter, the number of insoluble fine particles in the purified water was measured after the syringes were violently vibrated for 10 minutes. Table 6 shows the results.

TABLE 6

| | Number (piece) of insoluble fine particles per syringe | | |
|---|---|---|---|
| | Not less than 5 μm | Not less than 10 μm | Not less than 25 μm |
| Example 1 | 32 | 3 | 0 |
| Example 4 | 36 | 5 | 0 |
| Example 5 | 34 | 4 | 0 |
| Comparison example 1 | 40 | 6 | 0 |

(Experiment 6: Flow Rate Accuracy Evaluation Test Conducted by Using Syringe Pump)

By using a syringe pump (TE-331 produced by Terumo Corporation), the flow rate accuracy of each syringe was evaluated. The polypropylene (produced by Japan Polychem Corporation) used as a material forming outer cylinders for syringes was injection-molded to form the outer cylinders for the syringes each having the configuration shown in FIG. 5. The cylindrical portion of each of the outer cylinders for the syringes had an inner diameter of 29 mm and a length of 121 mm. The polypropylene (produced by Japan Polychem Corporation) used as a material forming plungers was injection-molded to form the plungers each having the configuration shown in FIG. 5.

The above-described outer cylinders for the syringes, the gaskets of the examples 1, 4, and 5 and the comparison example 1, and the above-described plungers were assembled to form syringes.

Thereafter, 40 ml of purified water was injected to each syringe barrel. After the sealing member was fitted on the distal end of the syringe barrel to seal it, autoclave sterilization was performed. Thereafter, each syringe was set on the syringe pump to discharge the purified water for eight hours at a flow rate of 5 ml/hour. By using an electronic balance, the weight of the discharged purified water was measured at intervals of 30 seconds. As a result, it has been confirmed that the gaskets of the examples 1 and 7 and the comparison example 1 stably discharged the purified water.

An exemplary medical appliance having the slidable coating layer is as described below.

(1) A medical appliance having a slidable coating layer which moves in contact with an inner surface of a medical member or that of a lumen and has said slidable coating layer formed at a part thereof which contacts said medical member or said lumen, wherein said slidable coating layer is formed of a composition containing solventless-type hardening silicone-based resin.

Exemplary embodiments may have the following forms:

(2) A medical appliance having a slidable coating layer according to the above (1), wherein said composition does not contain a tin-based compound.

(3) A medical appliance having a slidable coating layer according to the above (1) or (2), wherein said solventless-type hardening silicone-based resin has a viscosity of 30 to 500 mPa·s at 25 degrees C. before said solventless-type hardening silicone-based resin hardens.

(4) A medical appliance having a slidable coating layer according to any one of the above (1) through (3), wherein the solventless-type hardening silicone-based resin is a product of an addition reaction between silicone having at least two vinyl groups and a branch structure and silicone having at least two hydrogen groups bonded to the same silicon atom.

(5) A medical appliance having a slidable coating layer according to the above (4), wherein said silicone-based resin of said composition is formed by hydrosilylation between said vinyl groups of said silicone having said vinyl groups and said branch structure and silicon bonded to said hydrogen groups of said silicone having said hydrogen groups bonded to said silicon atom.

(6) A medical appliance having a slidable coating layer according to the above (4) or (5), wherein said silicone having said branch structure has a viscosity of 30 to 1,000 mPa·s at 25 degrees C.

(7) A medical appliance having a slidable coating layer according to any one of the above (4) through (6), wherein said silicone having said branch structure is formed by polymerizing 1,3,5,7-tetravinyltetramethylcyclotetrasiloxane and/or octamethylcyclotetrasiloxane with 1,5-diethenyl-3,3-bis[(ethenyldimethylsilyl)oxy]-1,1,5,5-tetramethylpentanetrisiloxane.

(8) A medical appliance having a slidable coating layer according to any one of the above (4) through (7), wherein said silicone having said hydrogen groups bonded to said silicon atom is a homopolymer or a copolymer of polymethylhydrosiloxane having a trimethylsilyl group at both terminals thereof.

(9) A medical appliance having a slidable coating layer according to any one of the above (4) through (7), wherein said silicone having said hydrogen groups bonded to said silicon atom is a homopolymer or a copolymer of polydimethylsiloxane having a hydrogen group at both terminals thereof.

(10) A medical appliance having a slidable coating layer according to any one of the above (1) through (9), wherein said composition contains a platinum group metal-based catalyst.

(11) A medical appliance having a slidable coating layer according to any one of the above (1) through (10), wherein said composition contains alkyl alkoxy silane or phenylalkoxysilane and in addition, glycidoxy alkyl alkoxysilane.

(12) A medical appliance having a slidable coating layer according to any one of the above (1) through (11), wherein said composition contains alkoxysilane having an ureido group or an uraren group or/and a product formed by a reaction between alkoxysilane having an amino group and a carboxylic anhydride.

(13) A medical appliance having a slidable coating layer according to any one of the above (1) through (12), wherein said coating layer does not contain solid fine particles and an emulsifier.

(14) A medical appliance having a slidable coating layer according any one of the above (1) through (13), wherein said solventless-type hardening silicone-based resin is thermosetting silicone-based resin.

(15) A medical appliance having a slidable coating layer according to any one of the above (1) through (14), wherein said coating layer has a thickness of 1 to 30 μm.

(16) A medical appliance having a slidable coating layer according to any one of the above (1) through (15), wherein said medical appliance is a guide wire or a catheter.

(17) A medical appliance having a slidable coating layer according to any one of the above (1) through (15), wherein said medical member is an outer cylinder for a syringe; said medical appliance is a gasket for said syringe slidably accommodated inside said outer cylinder for said syringe; and said gasket has a gasket body made of an elastic body and said slidable coating layer formed on a part thereof which contacts at least said outer cylinder for said syringe.

(18) A medical appliance having a slidable coating layer according to the above (17), wherein said medical member is a plastic outer cylinder for a syringe; and said medical appliance is a gasket for said plastic outer cylinder for said syringe.

An exemplary syringe is as described below.

(19) A syringe comprising an outer cylinder for said syringe; a gasket for said syringe which is a medical appliance, having a slidable coating layer, according to the above (17) or (18) and is slidably accommodated inside said outer cylinder; and a plunger which is mounted or can be mounted on said gasket.

(20) A syringe according to the above (19), wherein the syringe is filled with a liquid medicine.

(21) A syringe according to the above (19) or (20), wherein a dynamic sliding resistance value of said gasket is not more than 20 N when said gasket slides inside said outer cylinder at a low speed (100 mm/minute).

(22) A syringe according to any one of the above (19) through (21), wherein said outer cylinder is made of a plastic.

The detailed description above describes features and aspects of embodiments of a medical appliance with a slidable coating layer disclosed by way of example. The disclosure is not limited, however, to the precise embodiments and variations described. Various changes, modifications and equivalents could be effected by one skilled in the art without departing from the spirit and scope of the disclosure as defined in the appended claims. It is expressly intended that all such changes, modifications and equivalents which fall within the scope of the claims are embraced by the claims.

What is claimed is:

1. A medical appliance, comprising a slidable coating layer which moves while in contact with an inner surface of a medical member or an inner surface of a lumen,
   wherein said slidable coating layer is formed at a part of the medical appliance which contacts said medical member or said lumen,
   wherein said slidable coating layer is formed of a composition containing solventless hardening silicone-based resin.

2. The medical appliance having a slidable coating layer according to claim 1, wherein said composition does not contain a tin-based compound.

3. The medical appliance having a slidable coating layer according to claim 1, wherein said solventless hardening silicone-based resin has a viscosity of 30 to 500 mPa·s at 25° C. before said solventless hardening silicone-based resin hardens.

4. The medical appliance having a slidable coating layer according to claim 1, wherein said silicone-based resin of said composition is formed by hydrosilylation between said vinyl groups of said silicone having said vinyl groups and said branch structure and silicon bonded to said hydrogen groups of said silicone having said hydrogen groups bonded to said silicon atom.

5. The medical appliance having a slidable coating layer according to claim 1, wherein said silicone having said branch structure has a viscosity of 30 to 1,000 mPa·s at 25° C.

6. The medical appliance having a slidable coating layer according to claim 1, wherein said silicone having said branch structure is formed by polymerizing 1,3,5,7-tetravinyltetramethylcyclotetrasiloxane and/or octamethylcyclotetrasiloxane with 1,5-diethenyl-3,3-bis[(ethenyldimethylsilyl)oxy]-1,1,5,5-tetramethylpentanetrisiloxane.

7. The medical appliance having a slidable coating layer according to claim 1, wherein said silicone having said hydrogen groups bonded to said silicon atom is a homopolymer or a copolymer of polymethylhydrosiloxane having a trimethylsilyl group at both terminals thereof.

8. The medical appliance having a slidable coating layer according to claim 1, wherein said silicone having said hydrogen groups bonded to said silicon atom is a homopolymer or a copolymer of polydimethylsiloxane having a hydrogen group at both terminals thereof.

9. The medical appliance having a slidable coating layer according to claim 1, wherein said composition contains a platinum group metal-based catalyst.

10. The medical appliance having a slidable coating layer according to claim 1, wherein said composition contains alkyl alkoxy silane or phenylalkoxysilane and in addition, glycidoxy alkyl alkoxysilane.

11. The medical appliance having a slidable coating layer according to claim 1, wherein said composition contains alkoxysilane having an ureido group or an uraren group and/or a product formed by a reaction between alkoxysilane having an amino group and a carboxylic anhydride.

12. The medical appliance having a slidable coating layer according to claim 1, wherein said coating layer does not contain solid fine particles and an emulsifier.

13. The medical appliance having a slidable coating layer according to claim 1, wherein said solventless hardening silicone-based resin is a thermosetting silicone-based resin.

14. The medical appliance having a slidable coating layer according to claim 1, wherein said coating layer has a thickness of 1 to 30 μm.

15. The medical appliance having a slidable coating layer according to claim 1, wherein said medical appliance is a guide wire or a catheter.

16. The medical appliance having a slidable coating layer according to claim 1, wherein said medical member is an outer cylinder for a syringe,
   wherein said medical appliance is a gasket for said syringe slidably accommodated inside said outer cylinder for said syringe, and
   wherein said gasket has a gasket body made of an elastic body and said slidable coating layer formed on a part thereof which contacts at least said outer cylinder for said syringe.

17. The medical appliance having a slidable coating layer according to claim 16, wherein said medical member is a plastic outer cylinder for a syringe, and
   wherein said medical appliance is a gasket for said plastic outer cylinder for said syringe.

18. A syringe, comprising:
   an outer cylinder of said syringe;
   a gasket of said syringe which is the medical appliance having a slidable coating layer according to claim 16,
   wherein the gasket is slidably accommodated inside said outer cylinder.

19. The syringe according to claim 18, wherein the syringe is filled with a liquid medicine.

20. The syringe according to claim 18, wherein a dynamic sliding resistance value of said gasket is not more than 20 N when said gasket slides inside said outer cylinder at a low speed (100 mm/minute).

21. The syringe according to claim 18, wherein said outer cylinder is made of a plastic.

22. The syringe according to claim 18, further comprising a plunger which is mounted on said gasket.

* * * * *